US011519767B2

(12) United States Patent
Mahalingam et al.

(10) Patent No.: US 11,519,767 B2
(45) Date of Patent: Dec. 6, 2022

(54) DETERMINING FLUID PARAMETERS

(71) Applicant: Saudi Arabian Oil Company, Dhahran (SA)

(72) Inventors: Sakethraman Mahalingam, Aberdeen (GB); Muhammad Arsalan, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 73 days.

(21) Appl. No.: 17/014,805

(22) Filed: Sep. 8, 2020

(65) Prior Publication Data

US 2022/0074767 A1 Mar. 10, 2022

(51) Int. Cl.
| | | |
|---|---|---|
| *G01F 1/44* | (2006.01) | |
| *E21B 49/08* | (2006.01) | |
| *E21B 47/10* | (2012.01) | |
| *G01B 7/30* | (2006.01) | |
| *G01F 1/38* | (2006.01) | |

(Continued)

(52) U.S. Cl.
CPC .............. *G01F 1/44* (2013.01); *E21B 47/10* (2013.01); *E21B 49/0875* (2020.05); *G01B 7/30* (2013.01); *G01F 1/38* (2013.01); *G01N 9/32* (2013.01); *G01N 11/08* (2013.01); *G01N 33/2823* (2013.01)

(58) Field of Classification Search
CPC .......... G01F 1/38; G01F 1/44; E21B 49/0875; G01N 9/32
See application file for complete search history.

(56) References Cited

U.S. PATENT DOCUMENTS 2,643,723 A     6/1953   Lynes
2,964,285 A * 12/1960   Bardet .................... F16K 7/07
                                                                       251/5

(Continued)

FOREIGN PATENT DOCUMENTS

CN          101592475        12/2009
CN          201496028         6/2010

(Continued)

OTHER PUBLICATIONS

"Echo Dissolvable Fracturing Plug," EchoSeries, Dissolvable Fracturing Plugs, Gryphon Oilfield Solutions, Aug. 2018, 1 page.

(Continued)

*Primary Examiner* — John Fitzgerald
(74) *Attorney, Agent, or Firm* — Fish & Richardson P.C.

(57) ABSTRACT

A flow measurement assembly that includes a production string and a flow meter fluidically coupled to the production string. The flow meter includes a variable Venturi tube attached to and configured to flow production fluid received from the production string. The variable Venturi tube includes an end fixed to the production string and at least one Venturi throat. The flow meter also includes an actuator configured to move the variable Venturi tube with respect to the fixed end. The flow meter includes a processor communicatively coupled sensors coupled to the variable Venturi tube. The processor determines, based on a first fluid parameter and the second fluid parameter received from the sensors, at least one of a mass flow rate of the production fluid, a density of the production fluid, a viscosity of the production fluid, or a coefficient of discharge of the production fluid.

19 Claims, 8 Drawing Sheets

(51) Int. Cl.
  *G01N 9/32*    (2006.01)
  *G01N 11/08*   (2006.01)
  *G01N 33/28*   (2006.01)

(56) References Cited

U.S. PATENT DOCUMENTS

| | | | |
|---|---|---|---|
| 3,175,618 A | 3/1965 | Lang et al. | |
| 3,448,305 A | 6/1969 | Raynal et al. | |
| 3,558,936 A | 1/1971 | Horan | |
| 3,663,845 A | 5/1972 | Apstein | |
| 3,724,503 A | 4/1973 | Cooke | |
| 3,795,145 A | 3/1974 | Miller | |
| 3,894,563 A * | 7/1975 | Pausch | B01D 47/10 |
| | | | 138/45 |
| 3,906,792 A | 9/1975 | Miller | |
| 3,918,520 A | 11/1975 | Hutchison | |
| 3,970,877 A | 7/1976 | Russell et al. | |
| 4,096,211 A | 6/1978 | Rameau | |
| 4,224,687 A | 9/1980 | Claycomb | |
| 4,231,262 A * | 11/1980 | Boll | G01F 1/74 |
| | | | 73/861.04 |
| 4,387,318 A | 6/1983 | Kolm et al. | |
| 4,387,685 A | 6/1983 | Abbey | |
| 4,536,674 A | 8/1985 | Schmidt | |
| 4,685,523 A | 8/1987 | Paschal, Jr. et al. | |
| 4,757,709 A | 7/1988 | Czernichow | |
| 5,113,379 A | 5/1992 | Scherbatskoy | |
| 5,150,619 A | 9/1992 | Turner | |
| 5,224,182 A | 6/1993 | Murphy et al. | |
| 5,301,760 A | 4/1994 | Graham | |
| 5,317,223 A | 5/1994 | Kiesewetter et al. | |
| 5,375,622 A | 12/1994 | Houston | |
| 5,613,555 A | 3/1997 | Sorem et al. | |
| 5,693,891 A * | 12/1997 | Brown | G01F 1/36 |
| | | | 73/861.63 |
| 5,708,500 A | 1/1998 | Anderson | |
| 5,880,378 A | 3/1999 | Behring | |
| 5,892,860 A | 4/1999 | Maron et al. | |
| 5,965,964 A | 10/1999 | Skinner et al. | |
| 5,975,205 A | 11/1999 | Carisella | |
| 6,044,906 A | 4/2000 | Saltel | |
| 6,068,015 A | 5/2000 | Pringle | |
| 6,082,455 A | 7/2000 | Pringle et al. | |
| 6,193,079 B1 | 2/2001 | Weimer | |
| 6,209,652 B1 | 4/2001 | Portman et al. | |
| 6,339,963 B1 * | 1/2002 | Torkildsen | G01F 7/005 |
| | | | 73/861.63 |
| 6,504,258 B2 | 1/2003 | Schultz et al. | |
| 6,575,425 B1 * | 6/2003 | Betz | F16K 7/07 |
| | | | 251/5 |
| 6,578,638 B2 | 6/2003 | Guillory et al. | |
| 6,588,266 B2 | 7/2003 | Tubel et al. | |
| 6,622,574 B2 * | 9/2003 | Fincke | G01F 1/44 |
| | | | 702/50 |
| 6,629,564 B1 | 10/2003 | Ramakrishnan et al. | |
| 6,728,165 B1 | 4/2004 | Roscigno et al. | |
| 6,768,214 B2 | 7/2004 | Schultz et al. | |
| 6,779,601 B2 | 8/2004 | Wilson | |
| 6,857,920 B2 | 2/2005 | Marathe et al. | |
| 6,913,079 B2 | 7/2005 | Tubel | |
| 6,920,085 B2 | 7/2005 | Finke et al. | |
| 6,993,979 B2 | 2/2006 | Segeral | |
| 7,040,305 B2 * | 5/2006 | Sponton | F02M 26/19 |
| | | | 123/568.18 |
| 7,199,480 B2 | 4/2007 | Fripp et al. | |
| 7,224,077 B2 | 5/2007 | Allen | |
| 7,242,103 B2 | 7/2007 | Tips | |
| 7,249,805 B2 | 7/2007 | Cap | |
| 7,345,372 B2 | 3/2008 | Roberts et al. | |
| 7,410,003 B2 | 8/2008 | Ravensbergen et al. | |
| 7,668,411 B2 | 2/2010 | Davies et al. | |
| 7,847,421 B2 | 12/2010 | Gardner et al. | |
| 7,906,861 B2 | 3/2011 | Guerrero et al. | |
| 7,946,341 B2 | 5/2011 | Hartog et al. | |
| 8,047,232 B2 | 11/2011 | Bernitsas | |
| 8,258,644 B2 | 9/2012 | Kaplan | |
| 8,408,064 B2 | 4/2013 | Hartog et al. | |
| 8,421,251 B2 | 4/2013 | Pabon et al. | |
| 8,426,988 B2 | 4/2013 | Hay | |
| 8,464,582 B2 * | 6/2013 | Roux | G01F 1/44 |
| | | | 73/861.63 |
| 8,493,556 B2 | 7/2013 | Li et al. | |
| 8,564,179 B2 | 10/2013 | Ochoa et al. | |
| 8,604,634 B2 | 12/2013 | Pabon et al. | |
| 8,638,002 B2 | 1/2014 | Lu | |
| 8,648,480 B1 | 2/2014 | Liu et al. | |
| 8,786,113 B2 | 7/2014 | Tinnen et al. | |
| 8,916,983 B2 | 12/2014 | Marya et al. | |
| 8,925,649 B1 | 1/2015 | Wiebe et al. | |
| 8,948,550 B2 | 2/2015 | Li et al. | |
| 9,091,144 B2 | 7/2015 | Swanson et al. | |
| 9,106,159 B1 | 8/2015 | Wiebe et al. | |
| 9,109,429 B2 | 8/2015 | Xu et al. | |
| 9,130,161 B2 | 9/2015 | Nair et al. | |
| 9,140,815 B2 | 9/2015 | Lopez et al. | |
| 9,170,149 B2 | 10/2015 | Hartog et al. | |
| 9,239,043 B1 | 1/2016 | Zeas | |
| 9,321,222 B2 | 4/2016 | Childers et al. | |
| 9,322,389 B2 | 4/2016 | Tosi | |
| 9,499,460 B2 | 11/2016 | Kawamura et al. | |
| 9,581,489 B2 | 2/2017 | Skinner | |
| 9,599,460 B2 | 3/2017 | Wang et al. | |
| 9,599,505 B2 | 3/2017 | Lagakos et al. | |
| 9,617,847 B2 | 4/2017 | Jaaskelainen et al. | |
| 9,757,796 B2 | 9/2017 | Sherman et al. | |
| 9,784,077 B2 | 10/2017 | Gorrara | |
| 9,880,096 B2 | 1/2018 | Bond et al. | |
| 9,903,010 B2 | 2/2018 | Doud et al. | |
| 9,976,381 B2 | 5/2018 | Martin et al. | |
| 10,115,942 B2 | 10/2018 | Qiao et al. | |
| 10,209,383 B2 | 2/2019 | Barfoot et al. | |
| 10,352,125 B2 | 7/2019 | Frazier | |
| 10,367,434 B2 | 7/2019 | Ahmad | |
| 10,713,858 B2 * | 7/2020 | Mendible | G01F 25/10 |
| 11,045,777 B2 * | 6/2021 | Steckling | G05D 11/132 |
| 11,099,584 B2 * | 8/2021 | Shariff | E21B 43/121 |
| 2001/0036334 A1 | 11/2001 | Choa | |
| 2002/0043404 A1 | 4/2002 | Trueman et al. | |
| 2005/0033530 A1 * | 2/2005 | Stephenson | G01F 1/44 |
| | | | 702/45 |
| 2005/0047779 A1 | 3/2005 | Jaynes et al. | |
| 2006/0086498 A1 | 4/2006 | Wetzel et al. | |
| 2007/0012437 A1 | 1/2007 | Clingman et al. | |
| 2007/0062307 A1 * | 3/2007 | Jones | G01F 1/44 |
| | | | 73/861.63 |
| 2007/0181304 A1 | 8/2007 | Rankin et al. | |
| 2008/0048455 A1 | 2/2008 | Carney | |
| 2008/0100828 A1 | 5/2008 | Cyr et al. | |
| 2008/0277941 A1 | 11/2008 | Bowles | |
| 2009/0166045 A1 | 7/2009 | Wetzel et al. | |
| 2009/0304322 A1 | 10/2009 | Davies et al. | |
| 2010/0164231 A1 | 7/2010 | Tsou | |
| 2010/0224009 A1 * | 9/2010 | Steven | G01F 1/88 |
| | | | 73/861.42 |
| 2010/0300413 A1 | 12/2010 | Ulrey et al. | |
| 2010/0308592 A1 | 12/2010 | Frayne | |
| 2011/0049901 A1 | 3/2011 | Tinnen | |
| 2011/0088462 A1 | 4/2011 | Samson et al. | |
| 2011/0185805 A1 | 8/2011 | Roux et al. | |
| 2011/0273032 A1 | 11/2011 | Lu | |
| 2012/0018143 A1 | 1/2012 | Lembcke | |
| 2012/0211245 A1 | 8/2012 | Fuhst et al. | |
| 2012/0292915 A1 | 11/2012 | Moon | |
| 2013/0068481 A1 | 3/2013 | Zhou | |
| 2013/0091942 A1 | 4/2013 | Samson et al. | |
| 2013/0119669 A1 | 5/2013 | Murphree | |
| 2013/0167628 A1 | 7/2013 | Hull et al. | |
| 2013/0200628 A1 | 8/2013 | Kane | |
| 2013/0227940 A1 | 9/2013 | Greenblatt | |
| 2013/0255370 A1 | 10/2013 | Roux et al. | |
| 2014/0167418 A1 | 6/2014 | Hiejima | |
| 2014/0175800 A1 | 6/2014 | Thorp | |
| 2014/0208855 A1 | 7/2014 | Skinner | |
| 2014/0284937 A1 | 9/2014 | Dudley et al. | |

(56) References Cited

U.S. PATENT DOCUMENTS

| | | | |
|---|---|---|---|
| 2014/0311737 A1 | 10/2014 | Bedouet et al. | |
| 2015/0034580 A1 | 2/2015 | Nakao et al. | |
| 2015/0114127 A1 | 4/2015 | Barfoot et al. | |
| 2015/0318920 A1 | 11/2015 | Johnston | |
| 2016/0168957 A1 | 6/2016 | Tubel | |
| 2016/0177659 A1 | 6/2016 | Voll et al. | |
| 2016/0273947 A1 | 9/2016 | Mu et al. | |
| 2017/0033713 A1 | 2/2017 | Petroni | |
| 2017/0038246 A1 | 2/2017 | Coates et al. | |
| 2017/0075029 A1 | 3/2017 | Cuny et al. | |
| 2017/0235006 A1 | 8/2017 | Ellmauthaler et al. | |
| 2017/0260846 A1 | 9/2017 | Jin et al. | |
| 2018/0045543 A1 | 2/2018 | Farhadiroushan et al. | |
| 2018/0052041 A1 | 2/2018 | Yaman et al. | |
| 2018/0128661 A1 | 5/2018 | Munro | |
| 2018/0134036 A1 | 5/2018 | Galtarossa et al. | |
| 2018/0143048 A1* | 5/2018 | Lewis | G08B 21/182 |
| 2018/0155991 A1 | 6/2018 | Arsalan et al. | |
| 2018/0202843 A1 | 7/2018 | Artuso et al. | |
| 2018/0274311 A1 | 9/2018 | Zsolt | |
| 2018/0284304 A1 | 10/2018 | Barfoot et al. | |
| 2018/0347338 A1* | 12/2018 | Abbad | E21B 47/06 |
| 2018/0351480 A1 | 12/2018 | Ahmad | |
| 2019/0025095 A1 | 1/2019 | Steel | |
| 2019/0049054 A1 | 2/2019 | Gunnarsson | |
| 2019/0128113 A1 | 5/2019 | Ross et al. | |
| 2019/0253003 A1 | 8/2019 | Ahmad | |
| 2019/0253004 A1 | 8/2019 | Ahmad | |
| 2019/0253005 A1 | 8/2019 | Ahmad | |
| 2019/0253006 A1 | 8/2019 | Ahmad | |
| 2019/0376371 A1 | 12/2019 | Arsalan | |
| 2021/0207739 A1* | 7/2021 | Gomez | F01N 3/30 |
| 2022/0074304 A1* | 3/2022 | Mahalingam | G01F 1/44 |

FOREIGN PATENT DOCUMENTS

| | | |
|---|---|---|
| CN | 102471701 | 5/2012 |
| CN | 101488805 | 8/2012 |
| CN | 103913186 | 7/2014 |
| CN | 105043586 | 11/2015 |
| CN | 107144339 | 9/2017 |
| CN | 206496768 | 9/2017 |
| CN | 105371943 | 6/2018 |
| CN | 107664541 | 6/2018 |
| CN | 108534910 | 9/2018 |
| CN | 111750939 A * | 10/2020 |
| DE | 202012103729 | 10/2012 |
| EP | 0380148 | 8/1990 |
| EP | 2072971 | 6/2009 |
| EP | 2893301 | 5/2018 |
| GB | 2218721 | 11/1989 |
| JP | 2010156172 | 7/2010 |
| WO | WO 1993006331 | 4/1993 |
| WO | WO 2009030870 | 3/2009 |
| WO | WO 2009046709 | 4/2009 |
| WO | WO 2014116458 | 7/2014 |
| WO | WO 2015073018 | 5/2015 |
| WO | WO 2016111849 | 7/2016 |
| WO | WO 2016130620 | 8/2016 |
| WO | WO 2017146593 | 8/2017 |
| WO | WO 2018125071 | 7/2018 |
| WO | WO 2018145215 | 8/2018 |
| WO | WO 2019243789 | 12/2019 |

OTHER PUBLICATIONS

"TervAlloy Degradable Magnesium Alloys," Terves Engineered Response, Engineered for Enhanced Completion Efficiency, Feb. 2018, 8 pages.

Bao et al., "Recent development in the distributed fiber optic acoustic and ultrasonic detection," Journal of Lightwave Technology 35:16, Aug. 15, 2017, 12 pages.

Bybee et al., "Through-Tubing Completions Maximize Production," SPE-0206-0057, Society of Petroleum Engineers (SPE), Drilling and Cementing Technology, JPT, Feb. 2006, 2 pages.

Chen et al., "Distributed acoustic sensor based on two-mode fiber," Optics Express, 26:19, Sep. 17, 2018, 9 pages.

Corona et al., "Novel Washpipe-Free ICD Completion With Dissolvable Material," OTC-28863-MS, Offshore Technology Conference (OTC), presented at the Offshore Technology Conference, Apr. 30-May 3, 2018, 10 pages.

Cox et al., "Realistic Assessment of Proppant Pack Conductivity for Material Section," SPE-84306-MS, Society of Petroleum Engineers (SPE), presented at the SPE Annual Technical Conference and Exhibition, Oct. 5-8, 2003, 12 pages.

ejprescott.com (online), "Water, Sewer and Drain Fittings B-22, Flange Adaptors," retrieved from URL <https://www.ejprescott.com/media/reference/FlangeAdaptorsB-22.pdf> retrieved on Jun. 15, 2020, available on or before Nov. 2010 via wayback machine URL <http://web.archive.org/web/20101128181255/https://www.ejprescott.com/media/reference/FlangeAdaptorsB-22.pdf>, 5 pages.

Fornarelli et al., "Flow patterns and heat transfer around six in-line circular cylinders at low Reynolds number," JP Journal of Heat and Mass Transfer, Pushpa Publishing House, Allahabad, India, Feb. 2015, 11:1 (1-28), 28 pages.

Gillard et al., "A New Approach to Generating Fracture Conductivity," SPE-135034-MS, Society of Petroleum Engineers (SPE), presented at the SPE Annual Technical Conference and Exhibition, Sep. 20-22, 2010, 14 pages.

Gomaa et al., "Computational Fluid Dynamics Applied to Investigate Development and Optimization of Highly Conductive Channels within the Fracture Geometry," SPE-179143-MS, Society of Petroleum Engineers (SPE), Spe Production & Operations, 32:04, Nov. 2017, 12 pages.

Gomaa et al., "Improving Fracture Conductivity by Developing and Optimizing a Channels Within the Fracture Geometry: CFD Study," SPE-178982-MS, Society of Petroleum Engineers (SPE), presented at the SPE International Conference and Exhibition on Formation Damage Control, Feb. 24-26, 2016, 25 pages.

Govardhan et al., "Critical mass in vortex-induced vibration of a cylinder," European Journal of Mechanics B/Fluids, Jan.-Feb. 2004, 23:1 (17-27), 11 pages.

Juarez and Taylor, "Field test of a distributed fiber-optic intrusion sensor system for long perimeters," Applied Optics 46:11, Apr. 10, 2007, 4 pages.

Keiser, "Optical fiber communications," 26-57, McGraw Hill, 2008, 16 pages.

Kern el al., "Propping Fractures With Aluminum Particles," SPE-1573-G-PA, Society of Petroleum Engineers (SPE), Journal of Per. Technology, 13:6 (583-589), Jun. 1961, 7 pages.

Meyer et al., "Theoretical Foundation and Design Formulae for Channel and Pillar Type Propped Fractures—A Method to Increase Fracture Conductivity," SPE-170781-MS, Society of Petroleum Engineers (SPE), presented at the SPE Annual Technical Conference and Exhibition, Oct. 27-29, 2014, 25 pages.

Palisch et al., "Determining Realistic Fracture Conductivity and Understanding its Impact on Well Performance—Theory and Field Examples," SPE-106301-MS, Society of Petroleum Engineers (SPE), presented at the 2007 SPE Hydraulic Fracturing Technology Conference, Jan. 29-31, 2007, 13 pages.

Poollen et al., "Hydraulic Fracturing—FractureFlow Capacity vs Well Productivity," SPE-890-G, Society of Petroleum Engineers (SPE), presented at 32nd Annual Fall Meeting of Society of Petroleum Engineers, Oct. 6-9, 1957, published as Petroleum Transactions AIME 213, 1958, 5 pages.

Poollen, "Productivity vs Permeability Damage in Hydraulically Produced Fractures," Paper 906-2-G, American Petroleum Institute, presented at Drilling and Production Practice, Jan. 1, 1957, 8 pages.

Qin et al., "Signal-to-Noise Ratio Enhancement Based on Empirical Mode Decomposition in Phase-Sensitive Optical Time Domain Reflectometry Systems," Sensors, MDPI, 17:1870, Aug. 14, 2017, 10 pages.

Takahashi et al., "Degradation Study on Materials for Dissolvable Frac Plugs," URTEC-2901283-MS, Unconventional Resources Tech-

(56) References Cited

OTHER PUBLICATIONS nology Conference (URTC), presented at the SPE/AAPG/SEG Unconventional Resources Technology Conference, Jul. 23-25, 2018, 9 pages.

Tinsley and Williams, "A new method for providing increased fracture conductivity and improving stimulation results," SPE-4676-PA, Society of Petroleum Engineers (SPE), Journal of Petroleum Technology, 27:11, Nov. 1975, 7 pages.

Vincent, "Examining Our Assumptions—Have Oversimplifications Jeopardized our Ability to Design Optimal Fracture Treatments," SPE-119143-MS, Society of Petroleum Engineers (SPE), presented at the 2009 SPE Hydraulic Fracturing Technology Conference, Jan. 19-21, 2009, 51 pages.

Vincent, "Five Things You Didn't Want to Know about Hydraulic Fractures," ISRM-ICHF-2013-045, presented at the International Conference for Effective and Sustainable Hydraulic Fracturing: An ISRM specialized Conference, May 20-22, 2013, 14 pages.

Vysloukh, "Chapter 8: Stimulated Raman Scattering," 298-302, in Nonlinear Fiber Optics, 1990, 5 pages.

Walker et al., "Proppants, We Don't Need No Proppants—A Perspective of Several Operators," SPE-38611-MS, Society of Petroleum Engineers (SPE), presented at the 1997 Annual Technical Conference and Exhibition, Oct. 5-8, 1997, 8 pages.

Wang et al., "Rayleigh scattering in few-mode optical fibers," Scientific reports, 6:35844, Oct. 2016, 8 pages.

Yamate et al., "Optical Sensors for the Exploration of Oil and Gas," Journal of Lightwave Technology 35:16, Aug. 15, 2017, 8 pages.

Yu et al., "Borehole seismic survey using multimode optical fibers in a hybrid wireline," Measurement, Sep. 2018, 125:694-703, 10 pages.

PCT International Search Report and Written Opinion in International Appln. No. PCT/US2021/049390, dated Jan. 5, 2022, 16 pages.

\* cited by examiner

DETERMINING FLUID PARAMETERS

FIELD OF THE DISCLOSURE

This disclosure relates to flow measurement devices, in particular, to differential pressure flow meters.

BACKGROUND OF THE DISCLOSURE

Measuring fluid parameters such as mass flow rate is critical in multiple industries and applications. Fluid parameters can be measured in different ways. One way of measuring fluid parameters in upstream and downstream operations is by using a differential pressure flow meter. Such flow meters can measure fluid parameters to help ensure product quality and increase efficiency. Accurate fluid measurements are important in making decisions related to equipment operations, business operations, and maintenance. Methods and equipment for improving the accuracy of flow meters are sought.

SUMMARY

Implementations of the present disclosure include a flow measurement assembly that includes a production string and a flow meter. The production string is disposed within a wellbore. The flow meter is fluidically coupled to the production string. The flow meter includes a variable Venturi tube attached to and configured to flow production fluid received from the production string. The variable Venturi tube includes an end fixed to the production string and at least one Venturi throat. The flow meter also includes an actuator operationally coupled to the variable Venturi tube. The actuator is configured to move a wall of the variable Venturi tube with respect to the fixed end of the variable Venturi tube to change a position of the Venturi throat or a pitch angle of a wall of the variable Venturi tube. The controller is operationally coupled to the actuator. The flow meter also includes a processor communicatively coupled to the controller, and a plurality of sensors communicatively coupled to the processor. The sensors are coupled to the variable Venturi tube. A first sensor of the multiple sensors is coupled to a first portion of the variable Venturi tube upstream of the Venturi throat and a second sensor of the plurality of sensors is coupled to a second portion of the variable Venturi tube downstream of the Venturi throat. The first sensor detects and transmit, to the processor, a first fluid parameter of the production fluid flowing upstream of the throat and the second sensor configured to detect a second fluid parameter of the production fluid flowing downstream of the throat. The processor is configured to determine, based on the first fluid parameter and the second fluid parameter, at least one of a mass flow rate of the production fluid, a density of the production fluid, a viscosity of the production fluid, or a coefficient of discharge of the production fluid.

In some implementations, the flow meter further includes a pressure vessel coupled to the production string and disposed outside the variable Venturi tube. The pressure vessel is configured to retain fluid leaked through the variable Venturi tube. The actuator is attached to an exterior surface of the pressure vessel. The actuator is configured to receive instructions from an operator or a controller to change the position and cross section of the throat. In some implementations, the pressure vessel is attached, at a first end of the vessel, to a fluid outlet of a first section of the production string and is attached, at a second end of the vessel opposite the first end, to a fluid inlet of a second section of the production string. The variable Venturi tube includes a fluid inlet at the first end fluidically coupled to the fluid outlet of the first section of the production string, and includes a fluid outlet at the second end fluidically coupled to the fluid inlet of the second section of the production string.

Implementations of the present disclosure include a flow measurement device that includes a flexible tube fluidically coupled to and configured to flow fluid received from a pipe. The flexible tube including an end fixed to the pipe and a throat of reduced diameter. The throat resides between a first portion of the flexible tube converging along a flow direction of the fluid and a second portion of the flexible tube diverging along the flow direction of the fluid. The flow measurement device also includes an actuator coupled to the flexible tube. The actuator is configured to move a wall of the flexible tube with respect to the fixed end of the flexible tube to change a position and a cross section of the throat. The flow measurement device also includes multiple sensors coupled to the flexible tube. A first sensor of the multiple sensors is coupled to the first portion of the flexible tube and a second sensor of the multiple sensors is coupled to the second portion of the flexible tube. The first sensor is configured to detect at least one fluid parameter of the fluid flowing upstream of the throat and the second sensor is configured to detect at least one fluid parameter of the fluid flowing downstream of the throat.

In some implementations, the flow measurement device further includes a pressure vessel coupled to the pipe and disposed outside the flexible tube. The pressure vessel is configured to retain fluid leaked through the flexible tube. The actuator is attached to an exterior surface of the pressure vessel and configured to receive instructions from an operator or a controller to change the position and cross section of the throat. In some implementations, the pressure vessel is attached, at a first end of the vessel, to a fluid outlet of a first section of the pipe and is attached, at a second end of the vessel opposite the first end, to a fluid inlet of a second section of the pipe. The flexible tube includes a fluid inlet at the first end fluidically coupled to the fluid outlet of the first section of the pipe, and includes a fluid outlet at the second end fluidically coupled to the fluid inlet of the second section of the pipe.

In some implementations, the flow measurement device also includes a processor communicatively coupled to the multiple sensors. The controller determines, based on fluid parameters received from the sensors, at least one a mass flow rate of the fluid, a density of the fluid, a coefficient of discharge of the fluid, or a viscosity of the fluid. In some implementations, the processor is configured to determine, with the throat at a first position and based on the fluid parameters received from the plurality of sensors and based on an estimated density of the fluid and an estimated coefficient of discharge, a mass flow rate of the fluid. In some implementations, the processor is configured to determine, with the throat at a second position different than the first position and based on the determined mass flow rate of the fluid, a density of the fluid or a coefficient of discharge of the fluid. The processor is configured to determine, with the throat at a third position different than the first position and the second positon and based on the determined mass flow rate of the fluid and based on the determined density of the fluid or the coefficient of discharge of the fluid, the other of the density of the fluid or the coefficient of discharge of the fluid.

In some implementations, the flow measurement device is attached to a production string disposed within a wellbore. Two of the sensors reside at a common cross section of the flexible tube. The two sensors are spaced circumferentially by 90° from each other. The fluid parameters include a strain or pressure number from each of the two sensors, and the processor is configured to determine, based on a difference between the respective strain or pressure numbers of the two sensors, an angle of inclination of the flow measurement device with respect to a surface of the wellbore.

In some implementations, the flexible tube includes a bellow assembly defining a second throat of reduced diameter and disposed downstream or upstream of the throat of the flexible tube. The second throat resides between a third portion of the flexible tube converging along a flow direction of the fluid and a fourth portion of the flexible tube diverging along the flow direction of the fluid. The first portion includes an internal surface roughness different than an internal surface roughness of the third portion, and the sensors include a third sensor coupled to the third portion and a fourth sensor coupled to the fourth portion of the flexible tube, and the processor is configured to determine, based on a difference between the strain or pressure at the first portion and a strain or pressure at the third portion, a viscosity of the fluid.

In some implementations, the flexible tube defines a second throat of reduced diameter and disposed downstream or upstream of the throat of the flexible tube. The throat of the flexible tube defines an inner diameter substantially equal to an inner diameter of the second throat. The second throat is moved by the actuator with respect to the fixed end.

In some implementations, the actuator is configured to change an inner diameter of the throat, a pitch angle of the first portion, a length of the first portion, a pitch angle of the second portion, and a length of the second portion. In some implementations, the actuator is configured to change the pitch angle of the first portion, the length of the first portion, the pitch angle of the second portion, and the length of the second portion without altering a beta ratio of the flexible tube.

In some implementations, the actuator is configured to change, in side view, a shape of the flexible tube from a first shape to a second shape different than the first shape, and the plurality of sensors are configured to detect the fluid parameters with the flexible tube in the first shape, the second shape, and between the first shape and second shape.

In some implementations, the flow measurement device further includes a stiffening ring disposed around the flexible tube and forming, together with the flexible tube, the throat. The stiffening ring defines an inner diameter that is less than an inner diameter of the flexible tube, and the actuator includes a movable arm attached to the stiffening ring and configured to move the stiffening ring in a direction parallel and perpendicular with respect to a flow direction of the fluid to change a location and cross section of the throat.

In some implementations, the actuator is configured to change a beta ratio of the flexible tube by increasing or reducing the inner diameter of the stiffening ring.

In some implementations, the flexible tube includes a bellow assembly defining a second throat of reduced dimeter and a third throat of reduced diameter. The throat of the flexible tube is disposed between the second throat and the third throat and defines an inner diameter smaller than an inner diameter of the second throat and smaller than an inner diameter of the third throat.

In some implementations, the flexible tube includes a second end opposite the fixed end, the second end coupled to a dismantle flexible joint attached to the actuator. The actuator is configured to move a sleeve of the dismantle flexible joint along a direction parallel to the flow direction of the fluid to change the position and a cross section of the throat.

Implementations of the present disclosure include receiving, by a processor and from multiple sensors coupled to a variable Venturi tube arranged in a first position, fluid information. The variable Venturi tube is fluidically coupled to and configured to flow production fluid received from a production string. The variable Venturi tube includes an end fixed to the production string and a Venturi throat. The fluid information includes a strain or fluidic pressure at a first portion of the variable Venturi tube upstream of the Venturi throat and a strain or fluidic pressure at a second portion of the variable Venturi tube downstream of the Venturi throat. The method also includes determining, by the processor and based on the fluid information and on a at least one estimated parameter of the production fluid, a first fluid parameter of the production fluid. The method also includes, with the throat in a second position different than the first position, by the processor and from the plurality of sensors, second fluid information including a strain or fluidic pressure at the first portion of the variable Venturi tube and a strain or fluidic pressure at the second portion of the variable Venturi tube. The method also includes determining, based on the second fluid information and based on the determined first fluid parameter, a second fluid parameter of the fluid.

Implementations of the present disclosure also include receiving, by a processor and from multiple sensors coupled to a flexible tube, fluid information. The flexible tube is fluidically coupled to and configured to flow fluid received from a pipe. The flexible tube includes an end fixed to the pipe and a throat in a first position with respect to the fixed end. The throat resides between a first portion of the flexible tube converging along a flow direction of the fluid and a second portion of the flexible tube diverging along the flow direction of the fluid. The fluid information includes a strain or pressure at the first portion of the flexible tube and a strain or pressure at the second portion of the flexible tube. The method also includes determining, by the processor and based on the fluid information, a first fluid parameter of the fluid. The method also includes transmitting, from the processor to a controller operationally coupled to the throat, second position information including a second position of the throat different than the first position to change a position of the throat from the first position to the second position. The method also includes, with the throat in the second position, by the processor and from the plurality of sensors, second fluid information including a strain or pressure at the first portion of the flexible tube and a strain or pressure at the second portion of the flexible tube, and determining, based on the second fluid information, a second fluid parameter of the fluid.

In some implementations, the method further includes, after determining the second fluid parameter, transmitting, from the processor to the controller, third position information including a third position of the throat different than the first and second positions to change a position of the throat from the second position to the third position. The method also includes receiving, with the throat in the third position, by the processor and from the plurality of sensors, third fluid information including a strain or pressure at the first portion of the flexible tube and a strain or pressure at the second portion of the flexible tube. The method also includes determining, based on the third fluid information, a third fluid parameter of the fluid. In some implementations, determining the first fluid parameter includes determining the first fluid parameter based on multiple estimated fluid parameters, and determining the second fluid parameter includes demining the second fluid parameter based on the determined first fluid parameter and based on at least one of the plurality of estimated fluid parameters, and determining the third fluid parameter includes determining the third fluid parameter based on the determined first fluid parameter and based on the determined second fluid parameter.

In some implementations, the first fluid parameter includes a mass flow rate of the fluid and the plurality of estimated fluid parameters include an estimated density of the fluid and an estimated coefficient of discharge of the fluid, and determining the mass flow rate of the fluid includes determining the mass flow rate based on the estimated density of the fluid and based on the estimated coefficient of discharge of the fluid. The second fluid parameter includes a density of the fluid, and determining the density of the fluid includes determining the density based on the determined mass flow rate of the fluid and based on the estimated coefficient of discharge, and the third fluid parameter includes a coefficient of discharge of the fluid, and determining the coefficient of discharge of the fluid includes determining the coefficient of discharge based on the determined mass flow rate of the fluid and based on the determined density of the fluid.

In some implementations, transmitting the second position information includes transmitting instructions to change at least one of a pitch angle of the first portion, a pitch angle of the second portion, or a beta ratio of the flexible tube.

In some implementations, determining the first fluid parameter includes determining the first fluid parameter based on the fluid information, multiple estimated parameters of the fluid, and based on calibration data. In some implementations, the calibration data includes a first fluid parameter as a function of a second fluid parameter based on multiple pitch angles of the first portion of the flexible tube and with a constant beta ratio of the flexible tube, and the first fluid parameter includes one of a coefficient of discharge of a fluid or a viscosity of a fluid, and the second fluid parameter includes the other of the coefficient of discharge of a fluid or a viscosity of a fluid. In some implementations, the plurality of pitch angles includes a first pitch angle of the first portion, a second pitch angle of the first portion greater than the first pitch angle, and a third pitch angle of the first portion greater than the second pitch angle, and further including, before transmitting the second position information, determining, by the processor, the second position information based on a pitch angle of the plurality of pitch angles.

In some implementations, the method further includes, prior to receiving the fluid information, transmitting first position information to the controller to set the first position of the throat, the first position determined based on 70% of a maximum operating envelope of the flexible tube or of the flow meter.

In some implementations, the plurality of sensors include multiple strain sensors attached to an external surface of the flexible tube, and receiving the fluid information includes receiving multiple values including a strain of the external surface of the flexible tube at multiple locations along a length of the flexible tube. Determining the first fluid parameter includes determining the first fluid parameter based on a difference of at least two of the plurality of values.

In some implementations, the flexible tube includes a second throat downstream of the throat of the flexible tube. The throat of the flexible tube defines an inner diameter substantially equal to an inner diameter of the second throat. The second throat resides between a third portion of the flexible tube converging along a flow direction of the fluid and a fourth portion of the flexible tube diverging along the flow direction of the fluid, and the fluid information includes a strain or pressure at the third portion of the flexible tube and a strain or pressure at the fourth portion of the flexible tube. In some implementations, the first portion includes an internal surface roughness different than an internal surface roughness of the third portion. The method also includes, based on a difference between the strain or pressure at the first portion and a strain or pressure at the third portion, a viscosity of the fluid. In some implementations, determining the viscosity of the fluid includes determining, based on a predetermined coefficient of discharge as a function of viscosity at the first portion and a predetermined coefficient of discharge as a function of viscosity at the third portion, a viscosity of the fluid.

In some implementations, the controller is coupled to an actuator coupled to and configured to move a stiffening ring disposed around the flexible tube. The ring forms, together with the flexible tube, the throat. The stiffening ring defines an inner diameter less than an outer diameter of the flexible tube, and the actuator is configured to move the stiffening ring in a direction parallel and perpendicular with respect to a flow direction of the fluid to change the position and cross section of the throat, and transmitting the second position information to the controller includes transmitting instructions to the controller to trigger the actuator to move the stiffening ring.

In some implementations, the controller is coupled to an actuator coupled to and configured to move a dismantle flexible joint attached to a second end of the flexible tube opposite the fixed end. The actuator is configured to move a sleeve of the dismantle flexible joint along a direction parallel to the flow direction of the fluid to change the position of the throat, and transmitting the second position information to the controller includes transmitting instruction to the controller to trigger the actuator to move the second end of the flexible tube.

In some implementations, the flexible tube is disposed at or near a downhole end of a production string disposed within a wellbore. Two of the plurality of sensors reside at a common cross section of the flexible tube, each of the two sensors spaced circumferentially by 90° from each other, and the fluid information includes a strain or pressure number from each of the two sensors. The method further includes determining, by the processor, a difference between the respective strain or pressure number of the two sensors, and determining, based on the determined difference, an angle of inclination of the flexible tube with respect to a surface of the wellbore.

Implementations of the present disclosure also include a method that includes receiving, by a processor and from multiple sensors coupled to a variable Venturi tube arranged in a first position, fluid information. The fluid information includes a differential pressure of a fluid flowing through the flexible Venturi tube. The method also includes comparing the fluid information with a differential pressure threshold. The method also includes determining, based on the comparison, that the differential pressure of the fluid satisfies the threshold. The method also includes determining, based on the determination that the differential pressure satisfies the threshold, shape information including instructions required to change a shape of the variable Venturi tube. The method also includes transmitting, to a controller, the shape information. The controller is configured to control an actuator coupled to the variable Venturi tube based on the shape information to change a shape of the variable Venturi tube.

Implementations of the present disclosure also include a system that includes at least one processing device, and a memory communicatively coupled to the at least one processing device. The memory stores instructions which, when executed, cause the at least one processing device to perform operations that includes receive, from multiple sensors coupled to a flexible tube, fluid information. The flexible tube is fluidically coupled to and configured to flow fluid received from a pipe. The flexible tube includes an end fixed to the pipe and a throat in a first position with respect to the fixed end. The throat resides between a first portion of the flexible tube converging along a flow direction of the fluid and a second portion of the flexible tube diverging along the flow direction of the fluid. The fluid information includes a strain or pressure at the first portion of the flexible tube and a strain or pressure at the second portion of the flexible tube. The operations also include determining, based on the fluid information, a first fluid parameter of the fluid. The operations also include transmitting, to a controller operationally coupled to the throat, second position information including a second position of the throat different than the first position to change a position of the throat from the first position to the second position. The operations also include receiving, from the plurality of sensors, with the throat in the second position, second fluid information including a strain or pressure at the first portion of the flexible tube and a strain or pressure at the second portion of the flexible tube. The operations also include determining, based on the second fluid information, a second fluid parameter of the fluid.

In some implementations, the operations further include, after determining the second fluid parameter, transmitting, to the controller, third position information including a third position of the throat different than the first and second positions to change a position of the throat from the second position to the third position. The operations also include receiving, with the throat in the third position and from the plurality of sensors, third fluid information including a strain or pressure at the first portion of the flexible tube and a strain or pressure at the second portion of the flexible tube, and determining, based on the third fluid information, a third fluid parameter of the fluid.

In some implementations, determining the first fluid parameter includes determining the first fluid parameter based on multiple estimated fluid parameters, and determining the second fluid parameter includes demining the second fluid parameter based on the determined first fluid parameter and based on at least one of the plurality of estimated fluid parameters. Determining the third fluid parameter includes determining the third fluid parameter based on the determined first fluid parameter and based on the determined second fluid parameter.

DETAILED DESCRIPTION OF THE DISCLOSURE

The present disclosure describes a flow meter with a variable Venturi tube that increases the accuracy and operating envelope of the meter. The variable Venturi tube has a throat of reduced diameter to create a pressure differential in the fluid flowing through the meter. The flow meter has multiple sensors that detect the pressure differential and an actuator that changes the shape of the variable Venturi tube to change the pressure differential of the fluid. A processor can determine multiple fluid parameters based on the pressure differentials. Such fluid parameters include mass flow rate, density, coefficient of discharge, and viscosity. The shape of the Variable Venturi can be quickly changed during production based on the current and expected flow rates and other parameters of the fluid. The sensor data gathered at different shapes of the variable Venturi tube can be used to accurately determine and confirm parameters of production fluids of different characteristics.

Particular implementations of the subject matter described in this specification can be implemented so as to realize one or more of the following advantages. The flow meter of the present disclosure has multiple movable throats that increase the operating envelope of the flow meter and allow the metering of fluids with a broad range of flow rates. The flow meter of the present disclosure reduces or eliminates the cost of having to replace a fluid meter that, when the flow rate of the fluid changes, may not be able to reliably meter the fluid. For example, the flow meter of the present disclosure can eliminate a situation in which a conventional 4-inch wellbore meter needs to be replaced by a 6-inch wellbore meter when the flow rate goes up (e.g., during re-fracture of the wellbore). The variable Venturi can have a high turndown due to its large operating envelop, such as a turndown of about 50. Additionally, the variable Venturi tube can have throats of different roughness to measure accurately the viscosity of the fluid.

Figure 1:
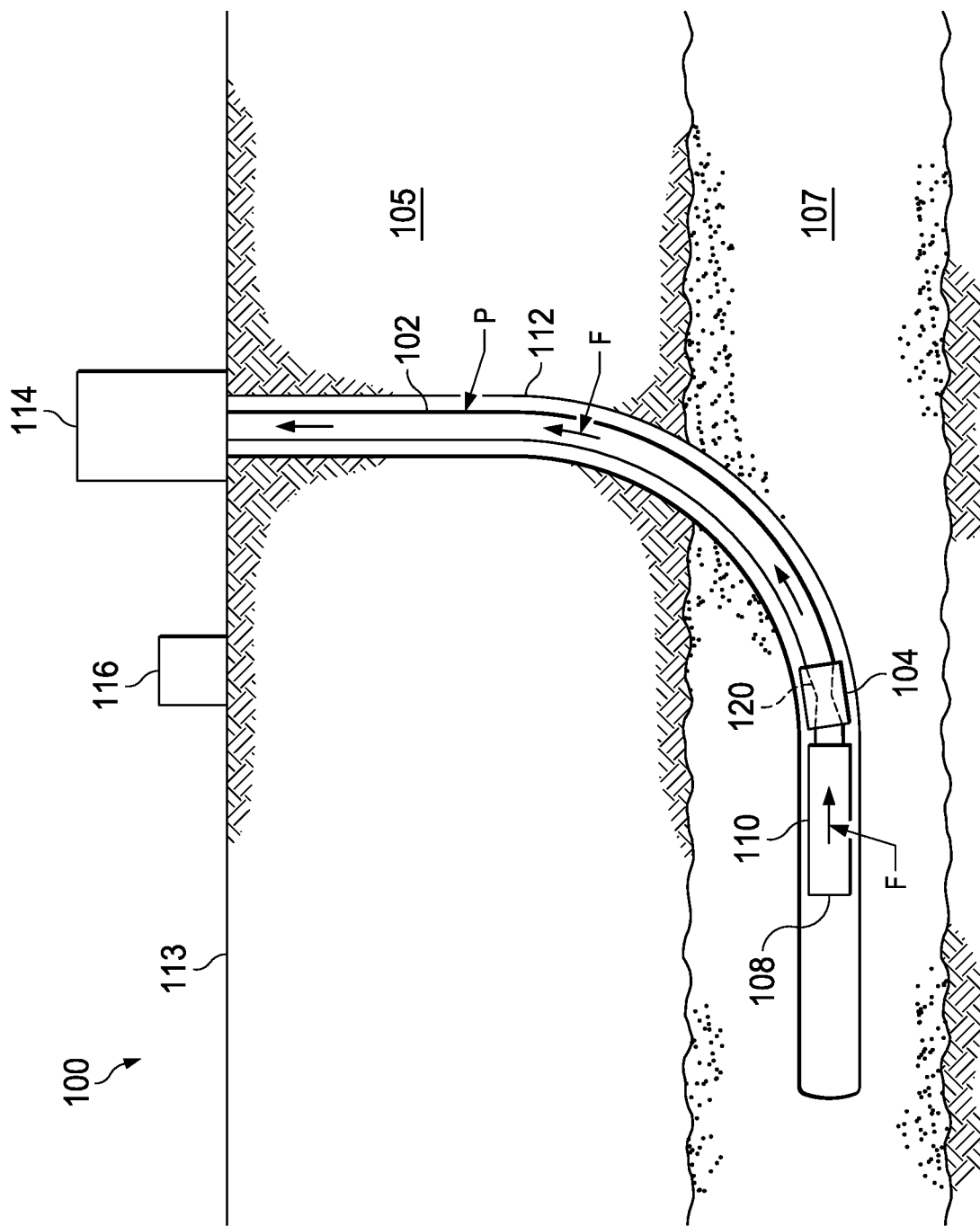
FIG. 1 is a front schematic view of a flow measurement assembly according to implementations of the present disclosure.

FIG. 1 shows a flow measurement assembly 100 that includes a production string 102 disposed within a wellbore 112 and a flow measurement device 104 (e.g., a flow meter) fluidically coupled to the production string 102. The wellbore 112 is formed in a geologic formation 105 that includes a hydrocarbon reservoir 107 from which hydrocarbons (e.g., production fluid 'F') can be extracted. The production string 102 is attached to a wellhead 114 that resides at a surface 113 (e.g., the land surface) of the wellbore 112. The production string 102 includes an electric submersible pump 110 (ESP) that can be attached to or near a downhole end 108 the production string 102. The ESP 110 flows the production fluid 'F' from the hydrocarbon reservoir 107 to the surface 113 of the wellbore 112. The flow meter 104 can be disposed uphole of the ESP 110 at or near the downhole end 108 of the production string 102. The flow meter 104 receives the production fluid 'F' from the ESP 110 to detect one or more parameters of the production fluid 'F'. The flow meter 104 can send the detected fluid information to a receiver 116 at the surface 113 of the wellbore 112. The receiver 116 can be connected to or be part of a processing device such as a processing device of a mobile computing device of an operator.

The flow meter 104 includes a flexible tube or variable Venturi tube 120 with a throat of reduced diameter that creates a pressure and velocity differential of the production fluid 'F' inside the tube 120. As further described in detail below with respect to FIGS. 2-5, the flow meter 104 has sensors that detect the pressure differential of the fluid 'F' inside the variable Venturi tube 120 to determine multiple parameters of the fluid 'F'. Although the flow meter 104 is shown implemented in a production operation of oil and gas, the flow meter 104 can be used in other applications such as in downstream operations, chemical plants, power plants, or any application in which accurate fluid measurements are required. In some implementations, the flow meter 104 can be attached to the production string 102 at a different location such as at or near the surface 113 of the wellbore 112 (e.g., downstream or upstream of the wellhead choke on the production flow line). Additionally, the flow meter 104 may be arranged in a horizontal or vertical orientation with respect to gravity.

The flow meter 104 can be communicatively coupled (e.g., with a wire or wirelessly) to the receiver 116 that receives information (e.g., the determined fluid parameters) from the flow meter 104.

Figure 2:
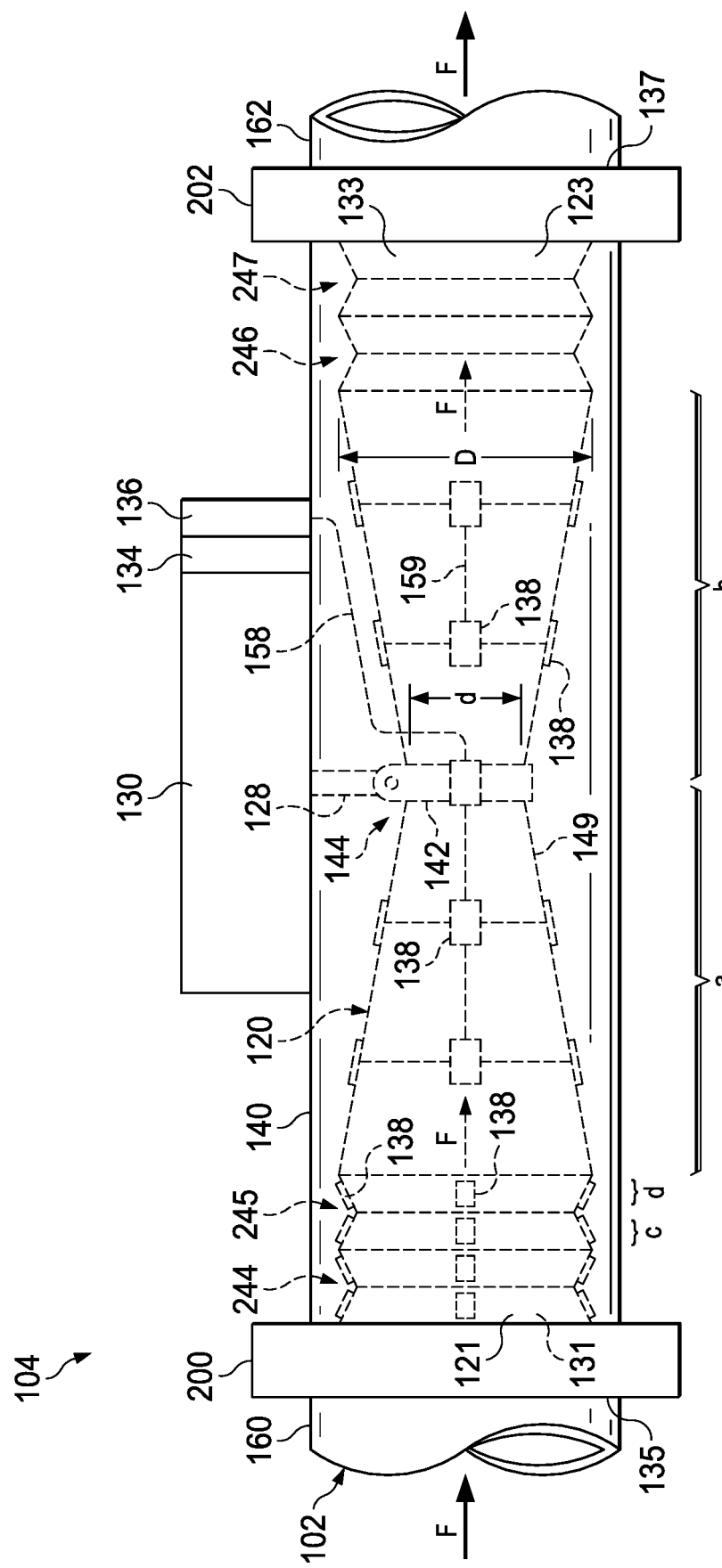
FIG. 2 is a front schematic view of a flow measurement device according to implementations of the present disclosure.

Referring to FIG. 2, the flow meter 104 includes a pressure vessel 140 attached to the production string 102. The pressure vessel 140 retains any fluid that may leak through the Venturi tube 120. The flow meter 104 is disposed between a first section 160 of the production string 102 and a second section 162 of the production string 102. The pressure vessel 140 has a first end 121 attached, with a first flange 200, to a fluid outlet 135 of the production string 102 and a second end 123 attached, with a second flange 202, to a fluid inlet 137 of the production string 102. The variable Venturi tube 120 is disposed inside and attached to the pressure vessel 140. The variable Venturi tube 120 has a first end 131 (e.g., a fluid inlet) that is fixed and fluidically coupled to the fluid outlet 135 of the first section 160 of the string 102, and a fluid outlet 133 that resides and is fluidically coupled to the fluid inlet 137 of the second section 162.

The flow meter 104 has a stiffening ring 142 disposed around the variable Venturi tube 120 that forms, together with the variable Venturi tube 120, a throat 144 of reduced diameter. The throat 144 has an inner diameter 'd' that is less than an inner diameter 'D' of the variable Venturi tube 120. The inner diameter 'D' of the tube 120 can be the inner diameter of the tube at its largest diameter or before and after the tapered portions of the tube. The flow meter 104 flows the production fluid 'F' from the fluid inlet 131, across the throat 144, to the fluid outlet 133 to detect parameters of the fluid.

Figure 3:
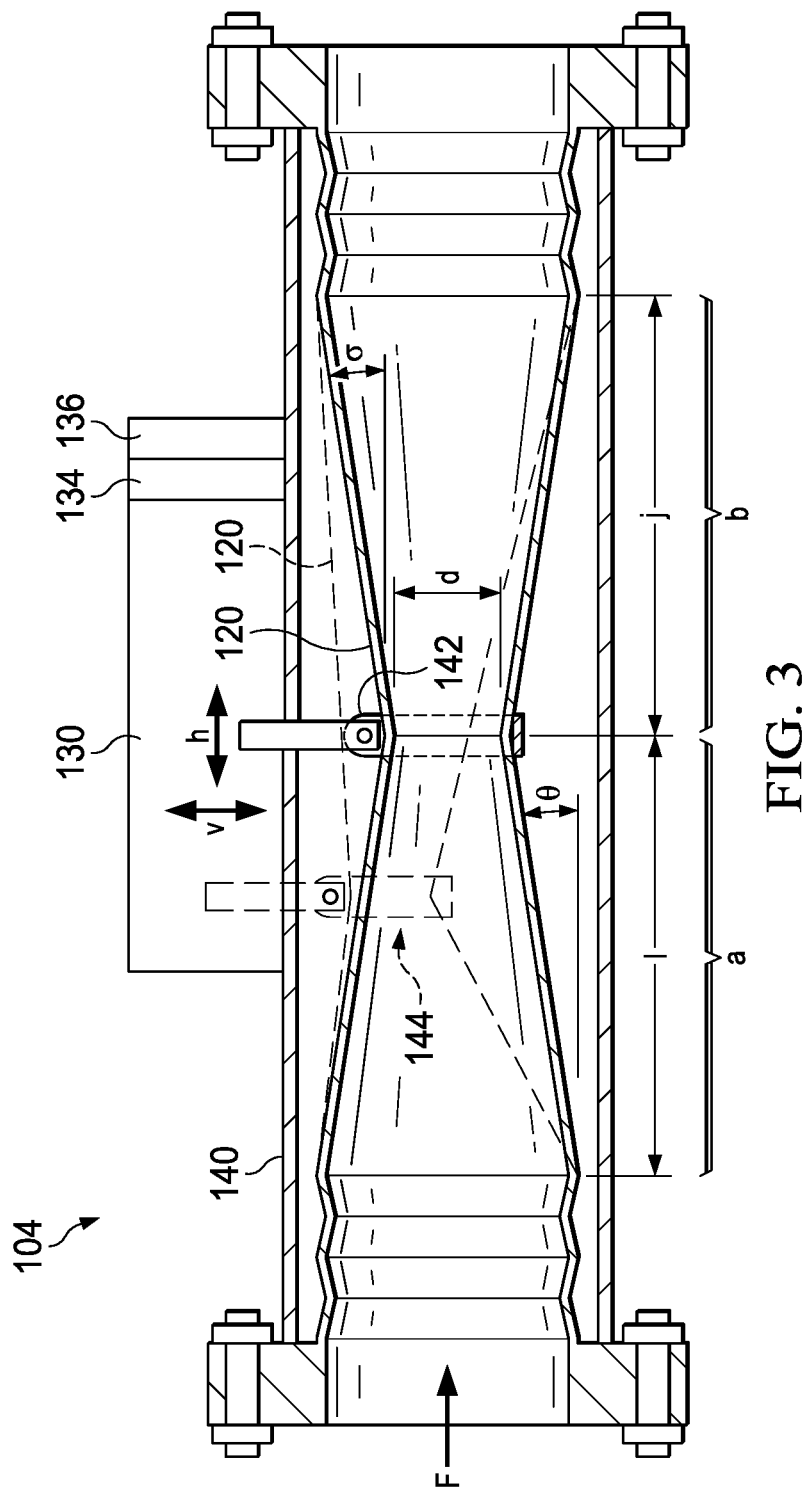
FIG. 3 is a front, partially cross-sectional view of the flow measurement device of FIG. 2.

The flow meter 104 also includes an actuator 130 (e.g., an electric actuator), a controller 134 electrically coupled to the actuator 130, and a processor 136 communicatively coupled to the controller 134. The actuator 130, processor 136, and controller 134 can be attached to an exterior surface of the pressure vessel 140. The actuator 130 can be controlled by the controller 134 or by an operator or technician. The actuator 130 is operationally coupled to the variable Venturi tube 120 to move a wall 149 of the Venturi tube 120 with respect to the fixed end 131 of the Venturi tube 120. Specifically, the actuator 130 has an arm 128 that extends through the pressure vessel 140 to a far end connected to the stiffening ring 142. Referring also to FIG. 3, the actuator 130 moves the stiffening ring 142 along a direction 'v' parallel to the flow direction of the fluid 'F' or along a direction 'h' perpendicular to the flow direction of the fluid 'F'. The actuator 130 moves the stiffening ring 142 to change the location or position of the throat 144. As further described in detail below with respect to FIG. 4, the actuator can also change a cross section of the throat. Such movements can change a pitch angle of the wall 149 and a beta ratio of the variable Venturi tube 120.

As shown in FIG. 2, the controller 134 is operationally coupled to the actuator 130 to trigger or control the actuator 130. The controller 134 and processor 136 can be a single device or two separate devices, as illustrated. The processor 136 receives fluid information from multiple sensors 138 (e.g., strain sensors) and uses the information to determine fluid parameters of the production fluid 'F'. An operator can use such parameters to make production, maintenance, and business-related decisions. Additionally, the processor can use such parameters to move the stiffening ring 142 to alter the dynamics of the fluid 'F' to re-determine or confirm fluid parameter of the fluid 'F'. Additionally, the processor 136 can be detached from the pressure vessel 140 and can be part of a computing device (e.g., a mobile device) that sends instructions to the controller 134.

The processor 136 can receive input (e.g., estimated fluid parameters and calibration data) from an operator. The flow meter 104 can be initially set manually (e.g., by an operator) based on an estimated flow rate provided at the time of installation. Subsequently, depending on the increase or decrease in differential pressure, the actuator 130 can automatically move to adjust the throat to suit the change. For example, the actuator 130 can change the shape or location or both of the throat to keep the differential pressure measurement within the 'sweet spot' of the flow meter 104 (e.g., within an optimal operational range of the sensors 138). The sensors 138 may not perform optimally if the differential pressure is too close to zero or is at the high end of the range of the sensor, so the actuator can change the position of the throat to accommodate to the operating range of the sensors 138. In some implementations, the position of the flow meter 104 may have to be verified manually periodically for verification or calibration with another sensor, for example, during a well test. In such cases, the actuator 130 can be operated manually to reset the flow meter based on the fresh calibration values.

The sensors 138 can be interconnected through a cable 159 and together communicatively connected, through a second cable 158 (or wirelessly) to the processor 136. The sensors 138 can be attached to an exterior surface of the wall 149 of the variable Venturi tube 120. The sensors 138 can be sensitive strain gauges that measure a strain of the wall 149 of the variable Venturi tube 120. In some implementations, the sensors 138 can be pressure sensors disposed inside the variable Venturi tube 120 and arranged to detect the fluidic pressure of the fluid 'F'. The sensors 138 can be distributed along the length of the variable Venturi tube 120. Additionally, the sensors 138 can be arranged by groups of two or more sensors that reside at a common cross section of the variable Venturi tube 120.

As shown in FIG. 2, groups of two or more sensors 138 are disposed at respective cross sections of the variable Venturi tube 120 and are spaced circumferentially by 90° from each other. For each group of sensors 138, each sensor can detect the same strain (e.g., when the flow meter 102 is arranged vertically) or a different strain (e.g., when the flow meter 103 is arranged horizontally) as the weight of the fluid within the Venturi tube 120 is additionally acting on the one sensor 138 disposed at the bottom of the fluid 'F'. Specifically, if the flexible Venturi flow meter is installed horizontally, the strain sensor 138 at the bottom and the strain sensor 138 that is 90° apart would read slightly different strains as the weight of the fluid within the pipe is additionally acting on the sensor underneath of the fluid 'F'. The processor 136 can use that information to infer the orientation of the flow meter and thus the angle of the wellbore. In some downhole applications, the pressure drop between a pair of sensors 138 within the flexible Venturi can be corrected for the hydrostatic weight of the fluid as the wellbore may be at an angle and not fully vertical. It is possible in those circumstances to use the circumferentially placed strain sensors 138 at various cross-sections to calculate the angle of the wellbore. For example, if the system is installed horizontally, likely any liquid content (moisture or heavier hydrocarbons) within the fluid will condense and flow at the bottom of the pipe causing a very small increase in pressure drop locally in the bottom compared to the top. This is because liquids have higher density and viscosity compared to gases. By plotting the strain/pressure measurements around the Venturi at any given cross-section, it may be possible to detect local pressure variations and correct for errors due to orientation or liquid drop-out from the flow.

The variable Venturi tube 120 has a first portion 'a' that converges along the flow direction of the fluid 'F' and a second portion 'b' that diverges along the flow direction of the fluid 'F'. The throat 144 resides between the first portion 'a' and the second portion 'b'. The first section 'a' resides upstream of the throat 144 and the second section 'b' resides downstream of the throat 144. At least one sensor 138 is coupled to the first portion 'a' of the Venturi tube 120 upstream of the throat 144 and at least one sensor 138 is coupled to the second portion 'b' of Venturi tube 120 downstream of the throat 144.

The sensor or sensors 138 at the first portion 'a' detect and transmit, to the processor 136, a first fluid parameter of the production fluid 'F' flowing upstream of the throat 144 and the sensor or sensors 138 at the second portion 'b' detect a second fluid parameter of the production fluid 'F' flowing downstream of the throat 144. The first and second fluid parameters can be respective strain or fluidic pressures. For example, as the fluid 'F' flows through a reduced cross section, the pressure of the fluid 'F' in the first portion 'a' increases and the pressure of the fluid 'F' in the second portion 'b' decreases. The fluidic pressure at the first portion 'a' causes the strain of the wall 149 of the first portion 'a' to increase with respect to the strain of the wall 149 of the second portion 'b'. Such strain differential can be used to compute a fluidic pressure differential between the fluid 'F' at the first portion 'a' and the fluid 'F' at the second portion 'b'. The processor 126 can use the determined pressure differential to determine multiple parameters of the fluid. For example, the processor can use the following formula of mass flow rate:

$$m_f = \frac{\varepsilon C_d A_t}{\sqrt{1-\beta^4}} \sqrt{2\rho_f \Delta P_f}$$

where $m_f$ is the mass flow rate of the fluid 'F', $\varepsilon$ is the expansibility of the fluid 'F' (e.g., when the fluid 'F' is a gas), Ca is the coefficient of discharge of the fluid 'F', $A_t$ is the cross sectional area of the throat 144, $\beta$ is the beta ratio of the Venturi tube 120, $\rho_f$ is the density of the fluid 'F', and $\Delta P_f$ is the differential pressure of the fluid 'F'.

Figure 4:
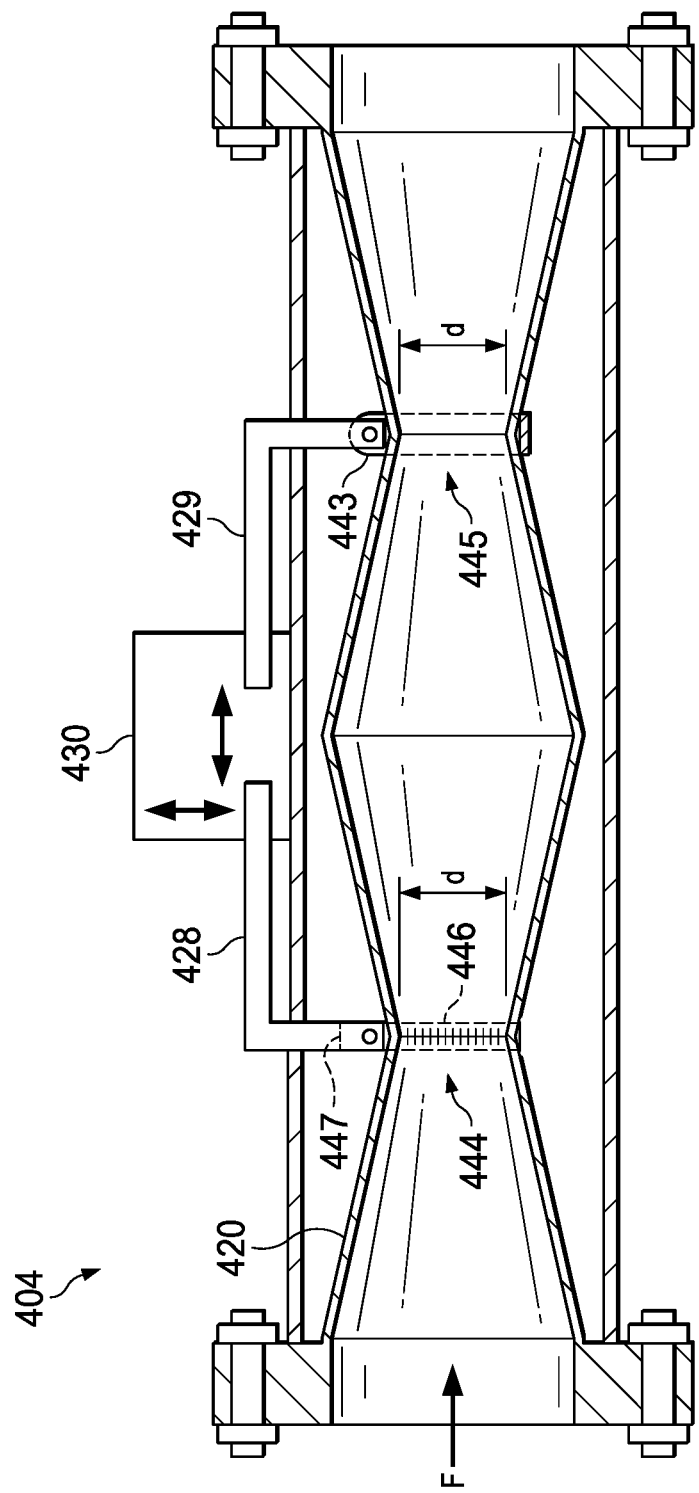
FIG. 4 is a front, partially cross-sectional view of a flow measurement device according to a second implementation of the present disclosure.

The coefficient of discharge of the fluid 'F' can be empirically determined. The density of the fluid 'F' can be initially estimated or based on a fluid measurement performed upstream of the flow meter 104, and the differential pressure of the fluid 'F' is determined based on the readings of the sensors 138. The cross sectional area of the throat 144 can be constant, as shown in FIGS. 2 and 3, or variable, as shown in FIG. 4.

As shown in FIG. 3, the stiffening ring 142 attached to the arm 128 of the actuator 130 can be fixed to the Venturi tube 120 so that horizontal movement of the stiffening ring 142 compresses one of the portions 'a' or 'b' of the tube 120 while the other one of the portions extends. In some implementations, the portions 'a' and 'b' can have a rigid shape so that movement of the portions 'a' and 'b' compresses or extends side throats 245 of the Venturi tube 120, or the portions 'a' and 'b' can be flexible so that movement compresses both the portions and the side throats 245. In some implementations, the stiffening ring can move along (e.g., roll along) the Venturi tube 120 so that horizontal movement of the stiffening ring 142 changes the shape of portions 'a' and 'b' without stretching the portions. The actuator 130 can be driven by a geared teeth arrangement in both directions. The processor 134 can include an encoder to know the precise position of the stiffening ring 142. Based on the position of the stiffening ring 142, the processor 136 can determine the entry and exit angles of the throat 144 (i.e., the angles of the portions 'a' and 'b').

As shown in FIG. 2, the beta ratio can be said to be the ratio between the smallest diameter (e.g., the inner diameter of the throat 144) seen by the fluid 'F' at the Venturi tube 120 and the inner diameter of the Venturi tube 120 before the convergent portion 'a' of the tube 120. For example, the beta ratio for the Venturi tube 120 in FIG. 2 is d/D. Thus, the beta ratio is a number between 0 and 1, and the smaller the beta ratio, the largest the difference between the pipe diameter and the throat diameter. The actuator 130 can change the beta ratio of the tube 120 by increasing or reducing the inner diameter of the stiffening ring 142.

Thus, the processor 136 can determine, based on the first fluid parameter (e.g., a first strain number) and the second fluid parameter (e.g., a second strain number), the mass flow rate of the fluid 'F'. As further described in detail below with respect to FIGS. 7-9, to determine the mass flow rate, the processor 129 can use estimated values for one or more parameters of the fluid 'F' (e.g., an estimated coefficient of discharge and an estimated density) to determine the mass flow rate of the fluid 'F'. Additionally, the processor can use an estimated mass flow rate of the fluid 'F' (or use a mass flow rate determined by another flow meter) to determine the density of the fluid. To estimate a density of the fluid 'F', the processing device 130 can use a predetermined relationship between differential pressure and different densities. For example, the equation described in Page 7 can provide the mass flow rate if the density of the fluid is known. From testing the meter 104 extensively (e.g., in lab conditions) with fluids of different densities, a curve between the second differential pressure (between exit and throat) and density of the fluid can be developed. It is theorized that such curve varies non-linearly. The processing device 130 can then use such information to determine or estimate a density of the fluid to obtain the mass flow rate.

In some embodiments, the flow meter 104 could use up to five strain/pressure measurements and hence providing four unique differential pressure measurements. In this case, one of the strain/pressure measurements can be made at the throat where the pressure will be the least. Two strain/pressure measurements can be made at the entry section, with a certain distance between the sensors 138 in the flow direction. The final two strain/pressure measurements can be made at exit section, again, with a certain distance between the sensors 138 in the flow direction. The differential pressures can be calculated with respect to the pressure at the throat, meaning the pressure at the throat can be subtracted from the other four pressure measurements to provide the four differential pressure measurements needed. The variation of each differential pressure with respect to the coefficient of discharge, mass flow rate, density and viscosity of the fluid can be empirically determined and used to determine such four parameters uniquely. Similar to the curve pressure vs density curve described above, the differential pressures with respect to the throat is likely to increase non-linearly with the mass flow rate, density and viscosity. The four differential pressures are likely to decrease non-linearly as a function of the coefficient of discharge. The coefficient of discharge is a fraction that is typically between 0.8 and 1.

Still referring to FIG. 2, the variable Venturi tube 120 can be a bellow assembly (e.g., made of one or more flexible tubular bellows) that is flexible to extend or contract along the flow direction of the fluid 'F'. Moving the bellows arrangement along the flow direction means that the natural flexibility in the bellows is used rather than causing increased strain when squeezing down on the throat 144 of the Venturi tube 120. The Venturi tube 120 can have multiple side throats 244, 245, 246, and 247 downstream and upstream of the middle throat 144. For example, the Venturi tube 120 can have two side throats 244 and 245 downstream of the convergent portion 'a' and two side throats 246 and 247 upstream of the divergent portion 'b'. The two side throats 244 and 245 downstream of the convergent portion 'a' can have the same inner diameter and the two side throats 246 and 247 upstream of the divergent portion 'b' can have the same inner diameter. Each of the side throats can have an inner diameter that is larger than the inner diameter 'd' of the middle throat 144. Sensors 138 can also be attached next to each side throat in a similar arrangement as the sensors 138 in portions 'a' and 'b'. The side throats 244, 245, 246, and 247 can have generally fixed inner diameters, while the middle throat 144 can move with respect to the side throats. The side throats may be implemented primarily to provide flexibility to adjust the length of Venturi tube when the middle throat 144 is moved about.

The side throat 245 adjacent the middle throat 144 resides between a third portion 'c' of the tube 120 that diverges along the flow direction of the fluid 'F' and a fourth portion 'd' that converges along the flow direction of the fluid 'F'. In some implementations, the first portion 'a' can have a different internal surface roughness than the second portion 'b', and the third portion 'c' can have an internal surface roughness that is different from an internal surface roughness of the first portion 'a' or 'b'.

Referring also to FIG. 3, the actuator 130 can change the inner diameter 'd' of the throat 144, a pitch angle 'θ' of the first portion 'a', a length 'l' of the first portion 'a', a pitch angle 'σ' of the second portion 'b', and a length 'j' of the second portion 'b'. The actuator 130 can change such dimensions without altering the beta ratio of the Venturi tube 120. The actuator 130 can move the stiffening ring 142 in all three dimensions: vertically along a direction 'v', horizontally along the flow direction of the fluid along direction 'h', and horizontally but in a direction perpendicular to the direction 'h'. Thus, the actuator 130 can change, in side view, top view, and front view, a shape of the Venturi tube from a first shape (shown in solid lines) to a second shape (shown in dashed lines) different from the first shape. The sensors 138 (shown in FIG. 2) detect the fluid parameters with the flexible tube in the first shape, in the second shape, and between the first shape and second shape.

FIG. 4 illustrates a flow meter 404 according to another implementation of the present disclosure. The flow meter 404 has a Venturi tube with a second throat 448 of reduced diameter that resides downstream (or upstream) of the first throat 444. The first throat 444 and second throat 445 can have substantially the same initial diameter 'd' and the actuator 430 can change the diameter and position of each throat 444 and 445. The actuator 430 has two arms 428 and 429 with each arm connected to respective stiffening rings 442 and 443. The first throat 444 can be moved similar to the throat 144 of FIGS. 2-3. The second arm 429 can also move the second stiffening ring 443 to move the second throat 445 along multiple directions, similar to the first throat 144 of FIGS. 2-3.

Referring to FIG. 4, one or both of the stiffening rings can be in form of or be replaced by a hose clamp 446 or hose clip that can be adjusted by a rotary drive 447 of the actuator 430 that rotates the screw of the hose clamp 446. The cross sectional area of the throat 444 and the beta ratio can of the Venturi tube be determined based on the movement of rotation of the drive 447 to increase or reduce the diameter of the hose clamp 446. As the screw of the house clamp 446 is tightened, the hose clip squeezes down on the Venturi tube 420 to reduce the diameter of the throat 444. The hose clamp 446 expands as the screw is loosened to increase the diameter of the throat 444. The diameter change may be between 5% and 30% of the original diameter of the Venturi tube 420, for example. The actuator 430 can be fitted with an encoder to measure how much the screw is turned and thus determine the area of the throat 444. The change in entry/exit angles ca be between about 1% and 25%. With multiple flexible Venturi throats 444 and 445, it is possible to have different angles in each of them.

In some implementations, the convergent section upstream of the first throat 444 can have an internal surface roughness different from the convergent section upstream of the second throat 445. The processor 430 can determine, based on a differential pressure along the Venturi tube 420, a viscosity of the fluid 'F'. For example, because of the relationship between fluid viscosity, surface roughness, and pressure, the processor 430 can determine the viscosity of the fluid 'F' based on the strain detected at the respective portions of the tube 420 that have different surface roughness. Generally, it is theorized that the larger the viscosity of the fluid, the more the surface roughness affects the velocity of the fluid, causing a decrease in fluidic pressure. The processor 430 can rely on a table or curve that relates fluidic pressure as a function of roughness for different fluid viscosities. The effect of surface roughness on pressure drop can be defined by the following Darcy-Weisbach equation:

$$\frac{\Delta P}{L} = \frac{(f \rho v^2)}{2D}$$

where ΔP is the pressure drop of the fluid 'F', L is the length of the flow line (e.g., the length of the Venturi tube), f is the friction factor (which is a function of surface roughness of the tube, fluid velocity, and fluid viscosity, in which the higher the viscosity the higher the friction factor and the higher the pressure drop), ρ is the density of the fluid 'F', v is the velocity of the fluid 'F', and D is the diameter of the pipe.

In some embodiments, a pipe segment of constant diameter but of different internal surface roughness can be disposed between the flow meter and the production line 160 (see FIG. 1). The pressure drop in such pipe can be measured using a differential pressure meter connected between the entry and exit section of such pipe segment. In other embodiments, the pipe segment can be used between the flow meter 104 and the production line section 162. In some implementations, determining the viscosity of the fluid 'F' includes determining, based on a predetermined coefficient of discharge as a function of viscosity at the section upstream of the first throat 444 and a predetermined coefficient of discharge as a function of viscosity at the section upstream of the second throat 445, a viscosity of the fluid 'F'.

Figure 5:
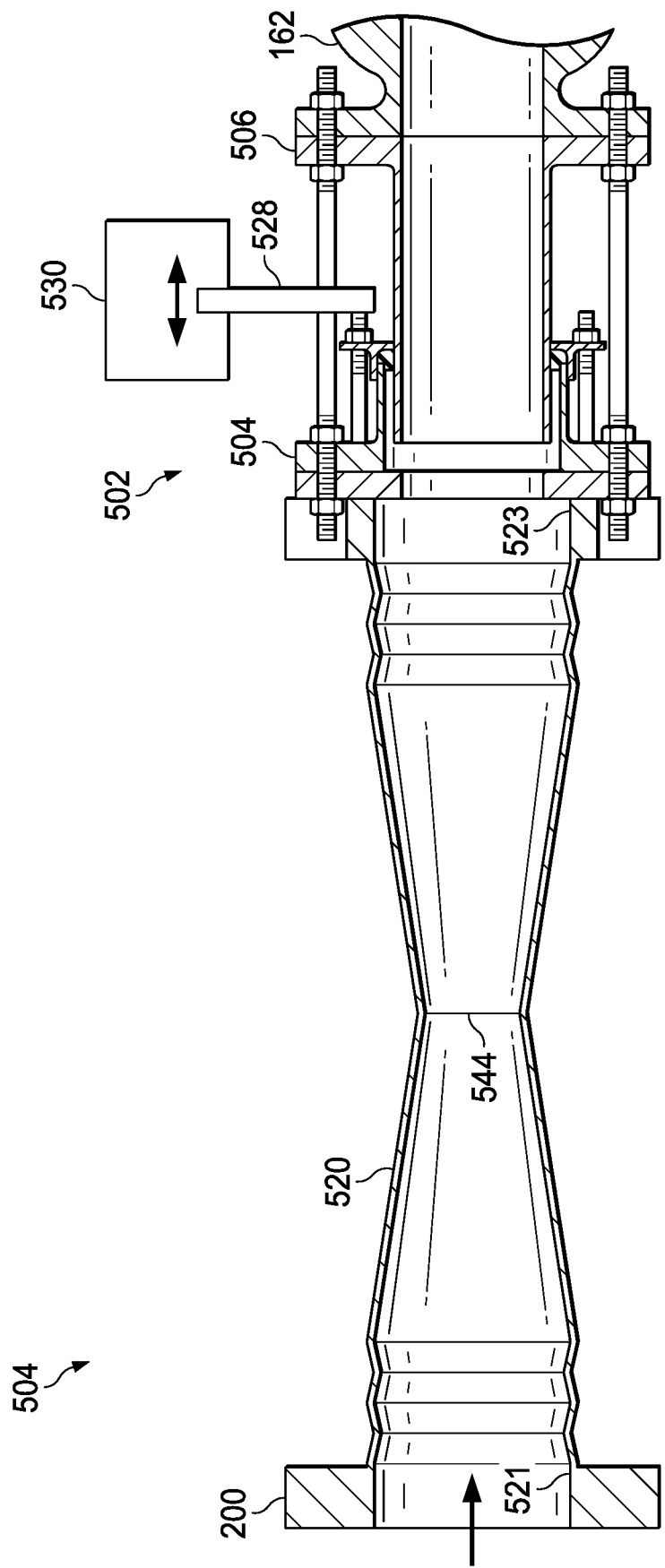
FIG. 5 is a front, partially cross-sectional view of a flow measurement device according to a third implementation of the present disclosure.

FIG. 5 shows a flow meter 504 according to another implementation of the present disclosure. The flow meter 504 does not have an external pressure vessel or housing. The flow meter 504 has a variable Venturi tube 520 that can have a wall toughness greater than the wall of the Venturi tube of FIGS. 2-4. The variable Venturi tube 520 is strong to resist a pressure of the production fluid 'F'. The Venturi tube 520 has a first end 521 fixed, through flange 200, to the production string and a second end 523 opposite the first end 521 that is attached to a dismantle flexible joint 502. The dismantle flexible joint 502 is attached to a portion 162 of the production string that does not move with respect to the flange 200. The dismantle flexible joint 502 has a tube 506 and a movable sleeve 504 disposed outside the tube 506. The sleeve 504 is arranged in a telescopic arrangement to move with respect to the tube 506 to extend or retract the dismantle flexible joint 502. The sleeve 504 is attached to an arm 528 of an actuator 530 that moves the sleeve 504 of the dismantle flexible along a direction parallel to the flow direction of the fluid 'F'. The movement of the dismantle flexible joint 502 compresses and expands the variable Venturi tube 520 to change the position and cross section of the throat.

The variable Venturi 520 may only be able to move parallel to the flow direction of the fluid 'F' without changing the diameter of the throat 544. For example, if the variable Venturi 540 is moved against the direction of flow, the middle throat 544 moves away from the dismantle flexible joint 502, the entry angle to the throat 544 increases and the exit angle of the throat decreases. These angles are defined with respect to the central longitudinal axis of the variable Venturi (extending parallel to the flow direction of the fluid 'F'). The flow meter 504 has multiple sensors inside or outside the variable Venturi tube 520. By changing the entry and exit angles, a new set of differential pressure measurements may be made and based on empirical tests. Such measurements can be used to calculate the coefficient of discharge as described in detail below with respect to FIG. 6. The diameter of the flexible bellows of the flow meter 504 may not be able to change.

Figure 6:
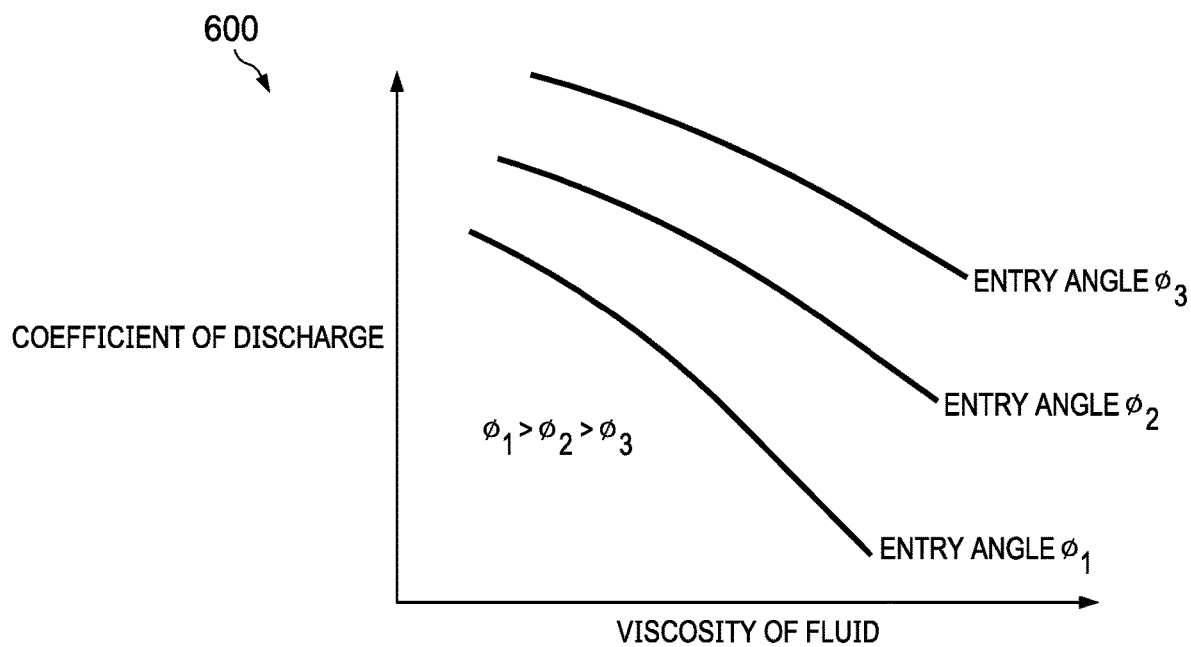
FIG. 6 is a plot of coefficient of discharge vs viscosity showing three curves representing entry angles of the flow measurement device.

FIG. 6 illustrates a plot 600 with multiple curves that are theorized to represent the coefficient of discharge as a function of the viscosity of the fluid for a throat of constant diameter but at three different entry angles $\phi_1$, $\phi_2$, and $\phi_3$. The entry angles are the pitch angles of the converging portions upstream of the throat. Specifically, the data of these curves can be used to calibrate the flow meter. For example, the flow meter can use the information of these curves to determine the viscosity of the fluid based on a known or estimated coefficient of discharge and a known angle of entry. Similarly, increased roughness in the converging portions of the throats can cause a reduction in the coefficient of discharge. Thus, the pressure drop at two or more different roughness levels may be used to calculate the viscosity of the fluid.

The coefficient of discharge can be an empirical parameter. The coefficient of discharge is a strong function of the viscosity of the fluids and the angle of entry. If two fluids with same density but different viscosities flowed at the same rate through the Venturi, the pressure drop would be higher for the more viscous fluid and the coefficient of discharge would be lower. A steeper entry angle would also make the pressure drop to go up. Thus, the sensors can be calibrated with fluids of different viscosities flowing at different entry angles (but with the same beta ratio) and the processor 136 can know the coefficient of discharge vs. viscosity relationship for various entry angles. Thus, it is possible to estimate the viscosity of fluid by measuring the pressure drop and hence the coefficient of discharge at least 2 different entry angles, with the assumption that the flow rate does not change within the short time that the measurement are made.

Figure 7:
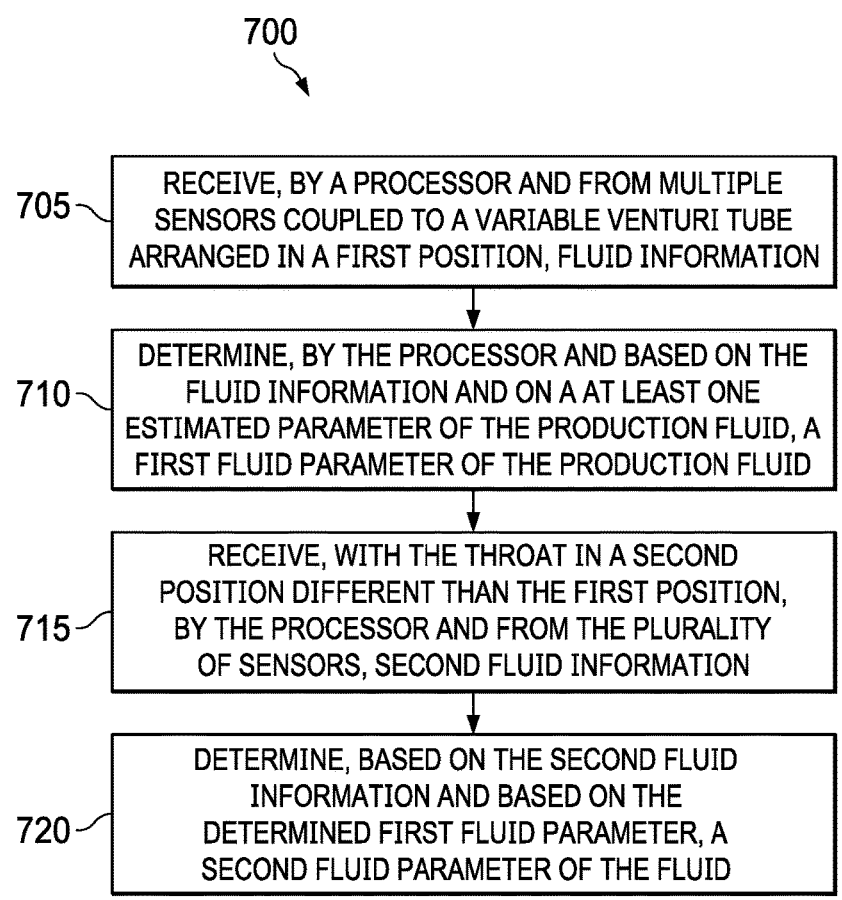
FIG. 7 is a flow chart of an example method of determining a fluid parameter.

FIG. 7 shows a flow chart of an example method 700 of determining a fluid parameter of a fluid. The method includes receiving, by a processor and from multiple sensors coupled to a variable Venturi tube arranged in a first position, fluid information. The variable Venturi tube is fluidically coupled to and configured to flow production fluid received from a production string. The variable Venturi tube has an end fixed to the production string and a Venturi throat. The fluid information includes a strain or fluidic pressure at a first portion of the variable Venturi tube upstream of the Venturi throat and a strain or fluidic pressure at a second portion of the variable Venturi tube downstream of the Venturi throat (705). The method also includes determining, by the processor and based on the fluid information and on at least one estimated parameter of the production fluid, a first fluid parameter of the production fluid (710). The method also includes receiving, with the throat in a second position different than the first position, by the processor and from the plurality of sensors, second fluid information including a strain or fluidic pressure at the first portion of the flexible tube and a strain or fluidic pressure at the second portion of the flexible tube (715). The method also includes determining, based on the second fluid information and based on the determined first fluid parameter, a second fluid parameter of the fluid (720).

Figure 8:
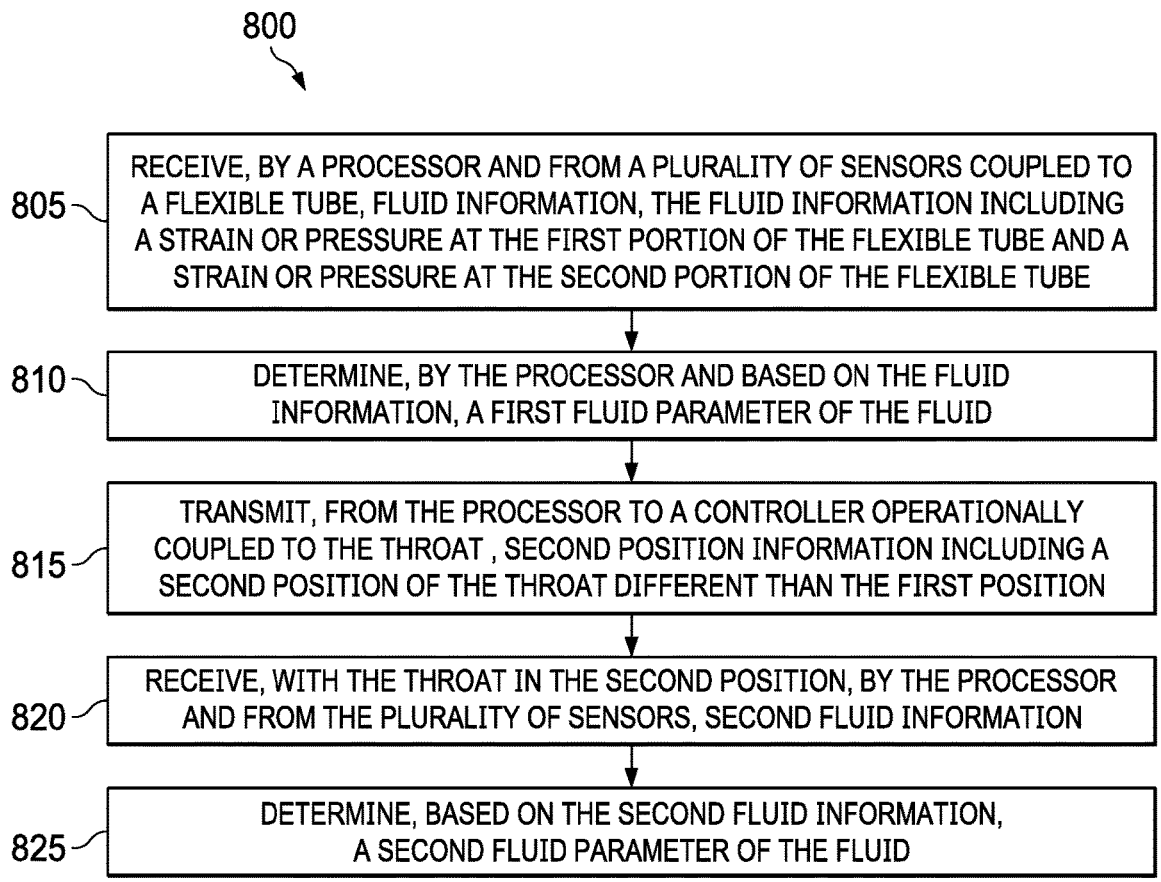
FIG. 8 is a flow chart of an example method of determining a fluid parameter according to another implementation of the present disclosure.

FIG. 8 shows a flow chart of an example method 800 of determining a fluid parameter of a fluid. The method includes receiving, by a processor and from a plurality of sensors coupled to a flexible tube, fluid information. The flexible tube is fluidically coupled to and configured to flow fluid received from a pipe. The flexible tube includes an end fixed to the pipe and a throat in a first position with respect to the fixed end. The throat resides between a first portion of the flexible tube converging along a flow direction of the fluid and a second portion of the flexible tube diverging along the flow direction of the fluid. The fluid information includes a strain or pressure at the first portion of the flexible tube and a strain or pressure at the second portion of the flexible tube (805). The method also includes determining, by the processor and based on the fluid information, a first fluid parameter of the fluid (810). The method also includes transmitting, from the processor to a controller operationally coupled to the throat, second position information including a second position of the throat different than the first position to change a position of the throat from the first position to the second position (815). The method also includes receiving, with the throat in the second position, by the processor and from the sensors, second fluid information including a strain or pressure at the first portion of the flexible tube and a strain or pressure at the second portion of the flexible tube (820). The method also includes determining, based on the second fluid information, a second fluid parameter of the fluid (825).

The method can be continued by transmitting, from the processor to the controller, third position information including a third position of the throat different than the first and second positions to change a position of the throat from the second position to the third position. The method can also include receiving, with the throat in the third position, by the processor and from the plurality of sensors, third fluid information including a strain or pressure at the first portion of the flexible tube and a strain or pressure at the second portion of the flexible tube, and determining, based on the third fluid information, a third fluid parameter of the fluid.

The turndown is the ratio of a flow meter's maximum to minimum flow rate. For example, a Venturi meter with the ability to measure a flow rate from 1 to 10 m³/hour has a turndown of 10. A turndown of 10 to 12 can be said to be typical for Venturi flow meters. By altering the throat diameter, entry/exit angles and surface roughness, the turndown of the meter can be about 50. For example, the flow meter may start with a beta ratio of 0.75 and, as the conditions change, the beta ratio can be changed to 0.6. Since the diameter has further reduced, the pressure drop at the throat with respect to the pressure at the entry section increases and hence, the processor can use the same strain/pressure sensors to compute an accurate differential pressure and mass flow rate. Altering the entry and exit angles, changing surface roughness and using multiple pressure/strain sensors allows the system to get more measurements from which additional fluid parameters such as density and viscosity may be computed. The flow meter of the present disclosure may achieve a flow rate from 1 to 50 m³/hr. The initial design of the flow meter may be set so that it can measure 70% of 50 m³/hour, which is equal to 35 m³/hr. The normal trend is that the flow from a well usually decreases with time. However, the flow in some wells may increase as well. Thus, 70% is a spot that allows for some meaningful room for change in either direction.

The first fluid parameter can be a mass flow rate of the fluid and the estimated fluid parameters can be an estimated density of the fluid and an estimated coefficient of discharge of the fluid. Determining the mass flow rate of the fluid includes determining the mass flow rate based on the estimated density of the fluid and based on the estimated coefficient of discharge of the fluid. The second fluid parameter can be a density of the fluid, and determining the density of the fluid includes determining the density based on the determined mass flow rate of the fluid and based on the estimated coefficient of discharge. Finally, the third fluid parameter can be a coefficient of discharge of the fluid, and determining the coefficient of discharge of the fluid includes determining the coefficient of discharge based on the determined mass flow rate of the fluid and based on the determined density of the fluid. Thus, the processor can determine and confirm the fluid parameters as the shape of the Venturi tube is modified.

Figure 9:
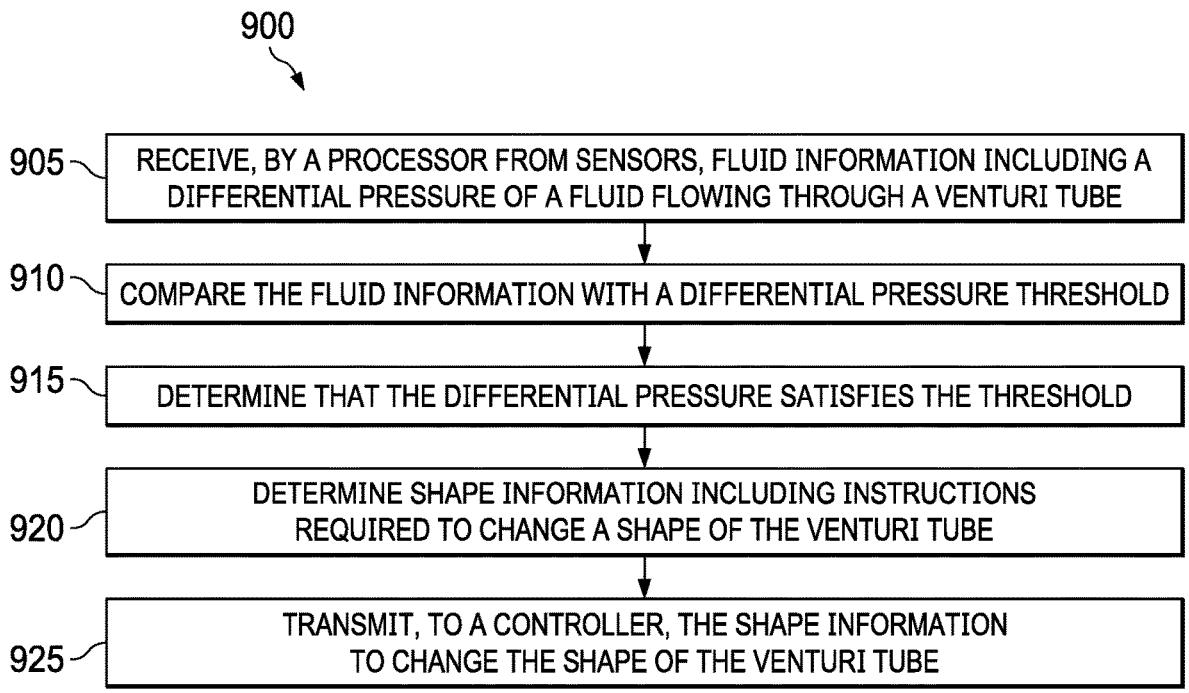
FIG. 9 is a flow chart of an example method of determining a shape of a Venturi tube.

By measuring pressure at multiple locations along the length, it is possible to use the differential pressure between every pair of pressure sensors to calculate or reconfirm the flow rate, density, viscosity, or coefficient of discharge of the fluid. The processor determines, with multiple throat shapes that cause multiple differential pressures, an accurate flow rate, density, viscosity, coefficient of discharge, and other parameters of the fluid. The processor can make corrections to the flow rate based and other parameters based on calibration data. FIG. 9 shows a flow chart of an example method 900 of changing a shape of the Venturi tube. The method includes receiving, by a processor and from multiple sensors coupled to a variable Venturi tube arranged in a first position, fluid information including a differential pressure of a fluid flowing through the flexible Venturi tube (905). The method also includes comparing the fluid information with a differential pressure threshold (910). The method also includes determining, based on the comparison, that the differential pressure of the fluid satisfies the threshold (915). The method also includes determining, based on the determination that the differential pressure satisfies the threshold, shape information including instructions required to change a shape of the variable Venturi tube (920). The method also includes transmitting, to a controller, the shape information, the controller configured to control an actuator coupled to the variable Venturi tube based on the shape information to change a shape of the variable Venturi tube (925).

For example, after initial conditions of throat diameter, entry/exit angle and position are inputted into the controller or the processor, the processor may determine that the pressure differential across the variable Venturi tube has decreased 5%, which meets the cut-off threshold (e.g., the differential pressure threshold). The processor then determines, based on the change in differential pressure, the amount of rotation that rotary drive (see rotary drive 447 in FIG. 4) requires to reduce the diameter of the hose clamp. The processor then sends the instructions to the controller to control the actuator to turn the rotary drive. In some implementations, the processor sends instructions to reduce the diameter of the throat until a differential pressure is detected that is back to normal. Then, the processor can detect the new throat diameter based on the turn angle of the hose clamp screw. Finally, the processor can calculate the flow rate of the fluid based on the new throat diameter and the differential pressure.

In implementations in which the throat diameter cannot be changed, such as in the flow meter shown in FIGS. 2 and 3, after initial conditions of throat diameter, entry/exit angle and position have been inputted into controller, the middle throat can be moved horizontally against the flow direction of the fluid. For example the middle throat can be moved a fixed distance (may be 5% of the length of the Venturi tube). Then, the processor determined the change in entry and exit angle based on the distance and direction of movement of the throat. Then, the processor determines the change in differential pressure between the throat and the entry section. Then under the assumption that viscosity of the fluid has not changed, the processor can use the curve in FIG. 6 to estimate the coefficient of discharge of the fluid. Finally, based on the determined coefficient of discharge, the processor can use the flow rate equation described above to determine the flow rate of the fluid.

Figure 10:
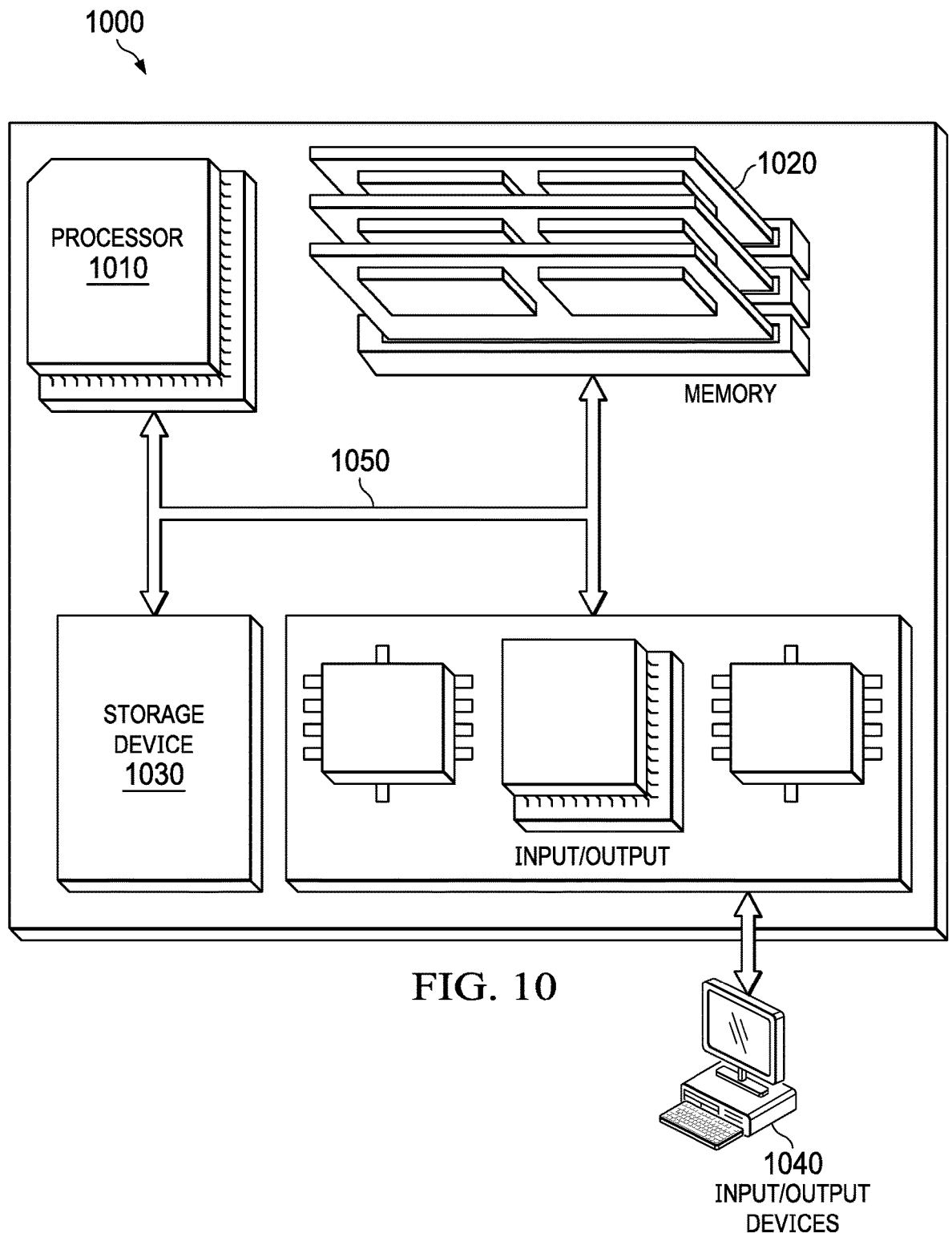
FIG. 10 shows an example controller or control system for a flow measurement device according to the present disclosure.

FIG. 10 is a schematic illustration of an example control system or controller for a flow meter according to the present disclosure. For example, the controller 1000 may include or be part of the controller 134 shown in FIG. 2 or may include or be part of the controller 134 and processor 136 shown in FIG. 2. The controller 1000 is intended to include various forms of digital computers, such as printed circuit boards (PCB), processors, digital circuitry, or otherwise. Additionally the system can include portable storage media, such as, Universal Serial Bus (USB) flash drives. For example, the USB flash drives may store operating systems and other applications. The USB flash drives can include input/output components, such as a wireless transmitter or USB connector that may be inserted into a USB port of another computing device.

The controller 1000 includes a processor 1010, a memory 1020, a storage device 1030, and an input/output device 1040. Each of the components 1010, 1020, 1030, and 1040 are interconnected using a system bus 1050. The processor 1010 is capable of processing instructions for execution within the controller 1000. The processor may be designed using any of a number of architectures. For example, the processor 1010 may be a CISC (Complex Instruction Set Computers) processor, a RISC (Reduced Instruction Set Computer) processor, or a MISC (Minimal Instruction Set Computer) processor.

In one implementation, the processor 1010 is a single-threaded processor. In another implementation, the processor 1010 is a multi-threaded processor. The processor 1010 is capable of processing instructions stored in the memory 1020 or on the storage device 1030 to display graphical information for a user interface on the input/output device 1040.

The memory 1020 stores information within the controller 1000. In one implementation, the memory 1020 is a computer-readable medium. In one implementation, the memory 1020 is a volatile memory unit. In another implementation, the memory 1020 is a non-volatile memory unit.

The storage device 1030 is capable of providing mass storage for the controller 1000. In one implementation, the storage device 1030 is a computer-readable medium. In various different implementations, the storage device 1030 may be a floppy disk device, a hard disk device, an optical disk device, or a tape device.

The input/output device 1040 provides input/output operations for the controller 1000. In one implementation, the input/output device 1040 includes a keyboard and/or pointing device. In another implementation, the input/output device 1040 includes a display unit for displaying graphical user interfaces.

Although the following detailed description contains many specific details for purposes of illustration, it is understood that one of ordinary skill in the art will appreciate that many examples, variations and alterations to the following details are within the scope and spirit of the disclosure. Accordingly, the exemplary implementations described in the present disclosure and provided in the appended figures are set forth without any loss of generality, and without imposing limitations on the claimed implementations.

Although the present implementations have been described in detail, it should be understood that various changes, substitutions, and alterations can be made hereupon without departing from the principle and scope of the disclosure. Accordingly, the scope of the present disclosure should be determined by the following claims and their appropriate legal equivalents.

The singular forms "a", "an" and "the" include plural referents, unless the context clearly dictates otherwise.

As used in the present disclosure and in the appended claims, the words "comprise," "has," and "include" and all grammatical variations thereof are each intended to have an open, non-limiting meaning that does not exclude additional elements or steps.

As used in the present disclosure, terms such as "first" and "second" are arbitrarily assigned and are merely intended to differentiate between two or more components of an apparatus. It is to be understood that the words "first" and "second" serve no other purpose and are not part of the name or description of the component, nor do they necessarily define a relative location or position of the component. Furthermore, it is to be understood that that the mere use of the term "first" and "second" does not require that there be any "third" component, although that possibility is contemplated under the scope of the present disclosure.

What is claimed is:

1. A flow measurement device comprising:
   a flexible bellow assembly fluidically coupled to and configured to flow fluid received from a pipe, the flexible bellow assembly comprising an end fixed to the pipe and a throat of reduced diameter, the throat residing between a first flexible portion of the flexible bellow assembly converging along a flow direction of the fluid and a second flexible portion of the flexible bellow assembly diverging along the flow direction of the fluid;
   an actuator coupled to the flexible bellow assembly, the actuator configured to move a wall of the flexible bellow assembly with respect to the fixed end of the flexible bellow assembly to change a cross section of the throat and a position of the throat such that the actuator moves the throat toward or away from the fixed end; and
   a plurality of sensors coupled to the flexible bellow assembly, a first sensor of the plurality of sensors coupled to the first flexible portion of the flexible bellow assembly and a second sensor of the plurality of sensors coupled to the second flexible portion of the flexible bellow assembly, the first sensor configured to detect at least one fluid parameter of the fluid flowing upstream of the throat and the second sensor configured to detect at least one fluid parameter of the fluid flowing downstream of the throat.

2. The flow measurement device of claim 1, wherein the flow measurement device is attached and in fluid communication with a downhole section of a production string disposed within a production wellbore.

3. The flow measurement device of claim 1, wherein the actuator comprises a movable arm fixed to the throat of the flexible bellow assembly such that horizontal movement of the arm compresses one of the first flexible portion or the second flexible portion and extends the other of the first flexible portion or the second flexible portion.

4. The flow measurement device of claim 1, wherein the actuator is configured to change, in side view, a shape of the flexible bellow assembly from a first shape to a second shape different than the first shape, and the plurality of sensors are configured to detect the fluid parameters with the flexible bellow assembly in the first shape, the second shape, and between the first shape and second shape.

5. The flow measurement device of claim 1, wherein the flexible bellow assembly comprises a second throat of reduced dimeter and a third throat of reduced diameter, the throat of the flexible bellow assembly disposed between the second throat and the third throat and defining an inner diameter smaller than an inner dimeter of the second throat and smaller than an inner diameter of the third throat.

6. The flow measurement device of claim 1, wherein the flexible bellow assembly comprises a second end opposite the fixed end, the second end coupled to a dismantle flexible joint attached to the actuator, the actuator configured to move a sleeve of the dismantle flexible joint along a direction parallel to the flow direction of the fluid to change the position and a cross section of the throat.

7. The flow measurement device of claim 1, further comprising a pressure vessel coupled to the pipe and disposed outside the flexible bellow assembly, the pressure vessel configured to retain fluid leaked through the flexible bellow assembly, wherein the actuator is attached to an exterior surface of the pressure vessel, the actuator configured to receive instructions from an operator or a controller to change the position and cross section of the throat.

8. The flow measurement device of claim 7, wherein the pressure vessel is attached, at a first end of the vessel, to a fluid outlet of a first section of the pipe and attached, at a second end of the vessel opposite the first end, to a fluid inlet of a second section of the pipe, and the flexible bellow assembly comprises a fluid inlet at the first end fluidically coupled to the fluid outlet of the first section of the pipe, and comprises a fluid outlet at the second end fluidically coupled to the fluid inlet of the second section of the pipe.

9. The flow measurement device of claim 1, further comprising a stiffening ring disposed around the flexible bellow assembly and forming, together with the flexible bellow assembly, the throat, the stiffening ring defining an inner diameter less than an inner diameter of the flexible bellow assembly, and wherein the actuator comprises a movable arm attached to the stiffening ring and configured to move the stiffening ring in a direction parallel and perpendicular with respect to a flow direction of the fluid to change a location and cross section of the throat.

10. The flow measurement device of claim 9, wherein the actuator is configured to change a beta ratio of the flexible bellow assembly by increasing or reducing the inner diameter of the stiffening ring.

11. The flow measurement device of claim 1, wherein the actuator is configured to change an inner diameter of the throat, a pitch angle of the first flexible portion, a length of the first flexible portion, a pitch angle of the second flexible portion, and a length of the second flexible portion.

12. The flow measurement device of claim 11, wherein the actuator is configured to change the pitch angle of the first flexible portion, the length of the first flexible portion, the pitch angle of the second flexible portion, and the length of the second flexible portion without altering a beta ratio of the flexible bellow assembly.

13. The flow measurement device of claim 1, further comprising a processor communicatively coupled to the plurality of sensors, the controller processor configured to determine, based on fluid parameters received from the sensors, at least one a mass flow rate of the fluid, a density of the fluid, a coefficient of discharge of the fluid, or a viscosity of the fluid.

14. The flow measurement device of claim 13, wherein the flow measurement device is attached to a production string disposed within a wellbore, two of the plurality of sensors reside at a common cross section of the flexible bellow assembly, the two sensors spaced circumferentially by 90° from each other, the fluid parameters include a strain or pressure number from each of the two sensors, and the processor is configured to determine, based on a difference between the respective strain or pressure numbers of the two sensors, an angle of inclination of the flow measurement device with respect to a surface of the wellbore.

15. The flow measurement device of claim 13, wherein the flexible a bellow assembly comprises a second throat of reduced diameter and disposed downstream or upstream of the throat, the second throat residing between a third flexible portion of the flexible bellow assembly converging along a flow direction of the fluid and a fourth flexible portion of the flexible bellow assembly diverging along the flow direction of the fluid, the first flexible portion comprises an internal surface roughness different than an internal surface roughness of the third flexible portion, and the plurality of sensors comprises a third sensor coupled to the third portion and a fourth sensor coupled to the fourth flexible portion of the flexible bellow assembly, and the processor is configured to determine, based on a difference between a strain or pressure at the first flexible portion and a strain or pressure at the third flexible portion, a viscosity of the fluid.

16. The flow measurement device of claim 13, wherein the flexible bellow assembly defines a second throat of reduced diameter and disposed downstream or upstream of the throat of the flexible bellow assembly, the throat of the flexible bellow assembly defining an inner diameter substantially equal to an inner diameter of the second throat, the second throat configured to be moved by the actuator with respect to the fixed end.

17. The flow measurement device of claim 13, wherein the processor is configured to determine, with the throat at a first position and based on the fluid parameters received from the plurality of sensors and based on an estimated density of the fluid and an estimated coefficient of discharge, a mass flow rate of the fluid.

18. The flow measurement device of claim 17, wherein the processor is configured to determine, with the throat at a second position different than the first position and based on the determined mass flow rate of the fluid, a density of the fluid or a coefficient of discharge of the fluid, and the processor is configured to determine, with the throat at a third position different than the first position and the second position and based on the determined mass flow rate of the fluid and based on the determined density of the fluid or the coefficient of discharge of the fluid, the other of the density of the fluid or the coefficient of discharge of the fluid.

19. A method comprising:
receiving, by a processor and from a plurality of sensors coupled to a flexible bellow assembly arranged in a first position, fluid information, the flexible bellow assembly fluidically coupled to and configured to flow fluid received from a pipe, the flexible bellow assembly comprising an end fixed to the pipe and a throat of reduced diameter, the throat residing between a first flexible portion of the flexible bellow assembly converging along a flow direction of the fluid and a second flexible portion of the flexible bellow assembly diverging along the flow direction of the fluid, wherein a first sensor of the plurality of sensors is coupled to the first flexible portion and a second sensor of the plurality of sensors is coupled to the second flexible portion, the first sensor configured to detect at least one fluid parameter of the fluid flowing upstream of the throat and the second sensor configured to detect at least one fluid parameter of the fluid flowing downstream of the throat, the fluid information comprising a strain or fluidic pressure at the first flexible portion upstream of the throat and a strain or fluidic pressure at the second flexible portion downstream of the throat;
determining, by the processor and based on the fluid information and on at least one estimated parameter of the fluid, a first fluid parameter of the fluid;

receiving, with the throat in a second position different than the first position, by the processor and from at least one sensors of the plurality of sensors, second fluid information including a strain or fluidic pressure at the first flexible portion and a strain or fluidic pressure at the second flexible portion, the throat moved to the second position by an actuator coupled to the flexible bellow assembly, the actuator configured to move a wall of the flexible bellow assembly with respect to the fixed end of the flexible bellow assembly to change a cross section of the throat and a position of the throat such that the actuator moves the throat toward or away from the fixed end; and determining, based on the second fluid information and based on the determined first fluid parameter, a second fluid parameter of the fluid.

\* \* \* \* \*